United States Patent
Bermudes et al.

(10) Patent No.: US 7,514,089 B2
(45) Date of Patent: *Apr. 7, 2009

(54) GENETICALLY MODIFIED TUMOR-TARGETED BACTERIA WITH REDUCED VIRULENCE

(75) Inventors: David Bermudes, Wallingford, CT (US); Kenneth Brooks Low, Guilford, CT (US)

(73) Assignee: Vion Pharmaceuticals, Inc., New Haven, CT (US)

(*) Notice: Subject to any disclaimer, the term of this patent is extended or adjusted under 35 U.S.C. 154(b) by 245 days.

This patent is subject to a terminal disclaimer.

(21) Appl. No.: 11/117,085

(22) Filed: Apr. 28, 2005

(65) Prior Publication Data

US 2007/0009489 A1    Jan. 11, 2007

Related U.S. Application Data

(60) Division of application No. 10/125,328, filed on Apr. 18, 2002, now Pat. No. 6,923,972, which is a continuation of application No. 09/337,689, filed on Jun. 22, 1999, now Pat. No. 6,475,482, which is a division of application No. 08/926,636, filed on Sep. 10, 1997, now Pat. No. 6,080,849.

(51) Int. Cl.
A61K 39/112 (2006.01)
C12N 15/00 (2006.01)
C07H 21/04 (2006.01)
C07K 14/255 (2006.01)
C12N 15/31 (2006.01)

(52) U.S. Cl. ............... 424/258.1; 424/235.1; 435/7.35; 435/252.8; 536/23.7

(58) Field of Classification Search ............... 424/235.1, 424/258.1, 93.2, 93.4; 435/252.3, 252.8
See application file for complete search history.

(56) References Cited

U.S. PATENT DOCUMENTS

| | | | |
|---|---|---|---|
| 4,436,727 A | 3/1984 | Ribi | |
| 5,021,234 A | 6/1991 | Ehrenfeld | |
| 5,318,900 A | 6/1994 | Habuka et al. | |
| 5,344,762 A | 9/1994 | Karapetian | |
| 5,705,151 A | 1/1998 | Dow et al. | |
| 5,824,538 A | 10/1998 | Branstrom et al. | |
| 5,830,702 A | 11/1998 | Portnoy et al. | |
| 5,877,159 A | 3/1999 | Powell et al. | |
| 5,997,881 A | 12/1999 | Powell et al. | |
| 6,051,237 A | 4/2000 | Paterson | |
| 6,080,849 A | 6/2000 | Bermudes et al. | |
| 6,143,551 A | 11/2000 | Goebel | |
| 6,150,170 A | 11/2000 | Powell et al. | |
| 6,190,657 B1 | 2/2001 | Pawelek et al. | |
| 6,251,406 B1 | 6/2001 | Haefliger et al. | |
| 6,410,012 B1 | 6/2002 | Sizemore et al. | |
| 6,447,784 B1 | 9/2002 | Bermudes et al. | |
| 6,475,482 B1 | 11/2002 | Bermudes et al. | |
| 6,537,558 B2 | 3/2003 | Kaniga | |
| 6,605,286 B2 | 8/2003 | Steidler et al. | |
| 6,685,935 B1 | 2/2004 | Pawelek et al. | |
| 6,863,894 B2 | 3/2005 | Bermudes et al. | |
| 6,923,972 B2 | 8/2005 | Bermudes et al. | |
| 6,955,953 B2 | 10/2005 | Yamazaki et al. | |
| 6,962,696 B1 | 11/2005 | Bermudes et al. | |
| 7,354,592 B2 | 4/2008 | Bermudes et al. | |
| 2001/0006642 A1 | 7/2001 | Steidler et al. | |
| 2001/0029043 A1 | 10/2001 | Haefliger et al. | |
| 2003/0059400 A1 | 3/2003 | Szalay et al. | |
| 2004/0229338 A1 | 11/2004 | King et al. | |
| 2005/0249706 A1 | 11/2005 | Bermudes et al. | |
| 2007/0298012 A1 | 12/2007 | King et al. | |

FOREIGN PATENT DOCUMENTS

| | | |
|---|---|---|
| AU | 719446 | 8/2000 |
| AU | 749695 | 10/2002 |
| AU | 783714 | 3/2006 |
| BR | PI-9609016-2 | 6/1996 |
| BR | PI 9812079-4 | 3/2000 |
| BR | 0014491-6 | 4/2002 |
| CA | 2224075 | 12/1997 |
| CA | 2302866 | 3/2000 |
| CA | 2386465 | 4/2002 |
| CN | 00816714.1 | 8/2000 |
| CN | ZL96196140.6 | 2/2004 |
| CN | ZL98811030.X | 4/2006 |
| EP | 00195672 | 9/1986 |
| EP | 0285152 | 3/1988 |
| EP | 0322237 | 6/1989 |
| EP | 0338679 | 10/1989 |

(Continued)

OTHER PUBLICATIONS

U.S. Appl. No. 08/846,422, filed Jun. 7, 1995, Yu, et al.
U.S. Appl. No. 10/732,570, filed Nov. 24, 2003, Pawelek, et al.
U.S. Appl. No. 09/724,390, filed Nov. 28, 2000, Bermudes, et al.
U.S. Appl. No. 11/064,533, filed Feb. 23, 2005, Bermudes, et al.
Brazilian Examiner's Report for Yale University, Brazilian App'l No. PI-9609016-2, Filed Jun. 5, 1996, Dated Jul. 18, 2006.
Mexican Search Report for Yale University, Mexican App'l No. 979439, Filed Dec. 3, 1997, Dated June 29, 2007.
Israeli Office Action for Yale University, et al., Israeli App'l No. 134946, Filed Jul. 3, 2000, Dated Apr. 11, 2007.
U.S. Office Action for Bermudes, et al., U.S. Appl. No. 11/064,533, filed Feb. 23, 2005, Dated Mar. 12, 2007.
U.S. Office Action for King, et al., U.S. Appl. No. 10/738,423, filed Dec. 16, 2003, Dated Jun. 28, 2007.

(Continued)

Primary Examiner—Phuong T Bui
(74) Attorney, Agent, or Firm—Law Offices of Albert Wal-Kit Chan, PLLC

(57) ABSTRACT

The present invention is directed to mutant *Salmonella* sp. having a genetically modified msbB gene in which the mutant *Salmonella* is capable of targeting solid tumors. The present invention further relates to the therapeutic use of the mutant *Salmonella* for growth inhibition and/or reduction in volume of solid tumors.

12 Claims, 11 Drawing Sheets

FOREIGN PATENT DOCUMENTS

Figure 4:
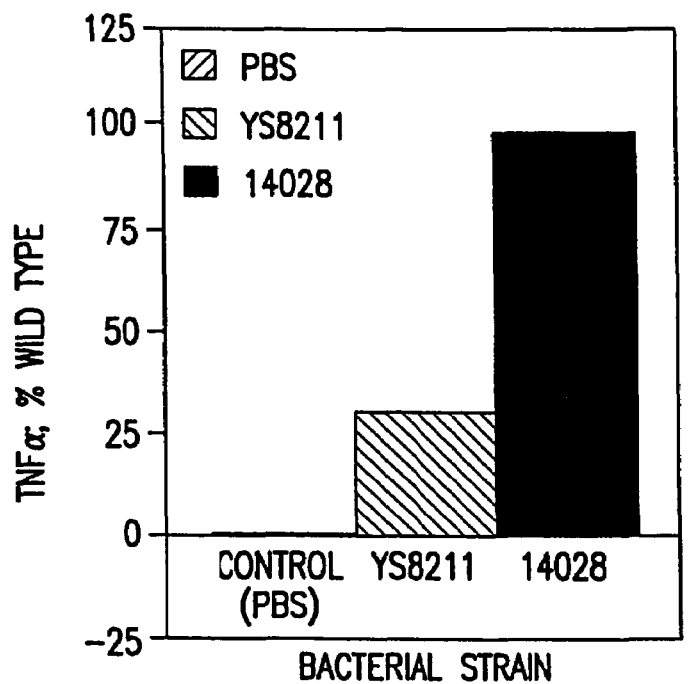

| | | |
|---|---|---|
| EP | 89302712.8 | 10/1989 |
| EP | 0357208 | 3/1990 |
| EP | 0400958 | 12/1990 |
| EP | 0564121 | 10/1993 |
| EP | 98 94 6891 | 9/1998 |
| EP | 1012232 A1 | 6/2000 |
| EP | 1261369 | 12/2002 |
| EP | 0833660 | 12/2006 |
| EP | 8833660 | 12/2006 |
| HK | 03108220.2 | 11/2003 |
| HK | 1017253 | 7/2004 |
| HK | 1033956 | 11/2006 |
| IL | 124936 | 7/2000 |
| IL | 148933 | 3/2002 |
| IL | 122407 | 12/2007 |
| JP | 62-145026 | 6/1987 |
| JP | 63-101328 | 5/1988 |
| JP | 01-180830 | 7/1989 |
| JP | 06046890 | 2/1994 |
| JP | 62-298657 | 10/1994 |
| JP | 2000-510842 | 3/2000 |
| JP | 2001-528552 | 4/2002 |
| JP | 2004-500042 | 4/2002 |
| JP | 3482213 | 10/2003 |
| KR | 7002535/2000 | 3/2000 |
| KR | 2002-7004371 | 4/2002 |
| KR | 0435932 | 6/2004 |
| MX | 979439 | 12/1997 |
| MX | 2000002355 | 3/2000 |
| MX | 2002/003384 | 4/2002 |
| MX | MX/A/2008/001378 | 1/2008 |
| NZ | 312341 | 9/1999 |
| NZ | 503376 | 2/2003 |
| NZ | 518354 | 2/2005 |
| SG | 51176 | 12/1998 |
| SG | 200201817-4 | 4/2002 |
| SG | 71486 | 4/2004 |
| WO | WO 91/06317 | 5/1991 |
| WO | WO 92/11361 | 7/1992 |
| WO | WO/92/15689 | 9/1992 |
| WO | WO 95/02048 | 1/1995 |
| WO | WO/95/05832 | 3/1995 |
| WO | WO/95/05835 | 3/1995 |
| WO | WO/95/09655 | 4/1995 |
| WO | WO 96/11277 | 4/1996 |
| WO | WO 96/14087 | 5/1996 |
| WO | WO 96/34631 | 11/1996 |
| WO | WO 96/40238 | 12/1996 |
| WO | WO/97/08955 | 3/1997 |
| WO | WO/97/18225 | 5/1997 |
| WO | WO 97/18837 | 5/1997 |
| WO | WO 97/19688 | 6/1997 |
| WO | WO 97/25061 | 7/1997 |
| WO | WO/98/53854 | 3/1998 |
| WO | WO 98/33923 | 8/1998 |
| WO | WO/98/53854 | 12/1998 |
| WO | WO/99/13003 | 3/1999 |
| WO | WO/99/13053 | 3/1999 |
| WO | WO 99/13053 | 3/1999 |
| WO | WO/99/52563 | 10/1999 |
| WO | WO/00/09733 | 2/2000 |
| WO | WO/01/25397 | 12/2001 |
| WO | WO/02/20809 | 3/2002 |
| ZA | 98/8289 | 5/1999 |

OTHER PUBLICATIONS

Bell, et al., 1990, "Molecular genetic analysis of an FNR-dependent anaerobically inducible *Escerichia coli* promoter," Molec. Microbiol. 4:1753-1763.

Bermudes, et al., 2000, "Tumor targetd Salmonella. Strain development and expression of the HSV TK effector gene," Gene Therapy, Methods and Protocols. 35: 419-436.

Bermudes, et al., 2000, "Tumor-targeted Salmonella. Highly selective delivery vectors", Advances in Exp. Med. And Bio. 465:47-63.

Boehm, et al., 1997, "Antiangiogenic therapy of experimental cancer does not induce acquired drug resistance," Nature 390(6658):404-407.

Chatfield et al., 1992, "Use of the nirB promoter to direct the stable expression of heterologous antigens in Salmonella oral vaccine strains: development of a single-dose oral tetanus vaccine," Biotechnology(NY) 10(8):888-892.

Chatfield et al., 1992, "Construction of a genetically defined *Salmonella typhi* Ty2 aroA, aroC mutant for the engineering of a candidate oral typhoid-tetanus vaccine," Vaccine 10(1):53-60.

Chen, et al., 1999, "Liposomes complexed to plasmids encoding angiostatin and endostatin inhibit breast cancer in nude mice," Cancer Res. 59 (14):Abstract only;.

Clark, S., 2001, "Diarrhoeagenic *Escherichia coli*-an emerging problem?" Diagnostic Microbiol. And Infect. Disease 41:93-98.

Curtiss, et al., 1989, "Selective delivery of antigens by recombinant bacteria," Curr Top Microbiol Immunol.146: 35-49.

Curtiss, 2002, "Bacterial infectious disease control by vaccine development," J. Clin. Invest. 110(8):1061-1066.

Darji, et al., 1997, "Oral Somatic Transgene Vaccine Using Attenuated *S. typhimurium*," Cell 91:765-775.

Deonarain, et al., 1995, "Genetic Delivery of Enzymes for Cancer Therapy", Gene Therapy, vol. 2, No. 4: 235-244.

Dietrich, et al., 1998, "Delivery of antigen-encoding plasmid DNA into the cytosol of macrophages by attenuated suicide Listeria monocytogenes," Nature Biotechnology 16:181-185.

Dietrich, et al., 2000, "Bacterial Systems for the Delivery of Eukaryotic Antigen Expression Vectors," Antisense & Nucleic Acid Drug Development 10:391-399.

Dinarello, et al., 1991, "Blocking IL-1:Interleukin-1 receptor antagonist in vivo and in vitro," Immunology Today 12(11):404-410.

Fairweather et al., 1990, "Use of live attenuated bacteria to stimulate immunity," Res. Microbiol. 141:769-773.

Fairweather et al., 1990 "Oral vaccination of mice against tetanus by use of a live attenuated salmonella carrier," Infect Immunity, 58:1323-1326.

Galan, et al., 1990, "Cloning and characterization of the asd gene of *Salmonella typhimurium*: use in stable maintenance of recombinant plasmids in Salmonella vaccine strains," Gene 94:29-35.

Galanos, et al., 1969, "A new method for the extraction of R, lipopolysaccharides," European J. Biochem. 9:245-249.

Gill, et al., 1996, "A malignant pleural effusion infected with *Salmonella enteridis*," Thorax 51(1):104-105.

Gonzalez, et al., 1994, "*Salmonella typhi* vaccine strain CVD 908 expressin the circumsporozoite protein of *Plasmodium falciparum*: strain construction and safety and immunogenicity in humans," J Infect Dis 169(4):927-31.

Grillot-Courvalin, et al., 1998, "Functional gene transfer from intracellular bacteria to mammalian cells," Nature Biotechnology 16:862-866.

Hakkaart et al., 1981, "Protein H encoded by plasmid Clo DF13 involved in lysis of the bacterial host. II. Functions and regulation of synthesis of the gene H product," Mol Gen Genet 183:326-332.

Hohmann, et al., 1996, "phoP/phoQ-deleted *Salmonella typhi* (Ty800) is a safe and immunogenic single-dose typhoid fever vaccine in volunteers," J Infect Dis 173(6):1408-1414.

Hohmann, et al., 1996, "Evaluation of a phoP/phoQ-deleted, aroA-deleted live oral *Salmonella typhi* vaccine strain in human volunteers," Vaccine 14:19-24.

Huber, et al., 1994, "Metabolism of 5-fluorocystine to 5-fluorouracil in human colorectal tumor cells transduced with the cytosine deaminase gene: significant antitumor effects when only a small percentage of tumor cells express cytosine deaminase," Proc. Natl. Acad. Sci. USA 91:8302-8306.

Jain, et al., 2001, "Use of bacteria as anticancer agents," Exp. Opin. Biol. Ther. 1(2):291-300.

Jayamaran, et al., 1988, "The nirB promoter of escherischia coli:location of nucleotide sequences essential for regulation by oxygen, the FNR protein and nitrite", Molec. Microbiol. 2:527-530.

King, et al., 2000, "Tumor Therapy using Salmonella", Emerging Drugs, 5:211-219.

Levine, et al., "Safety, infectivity, immunogenicity, and in vivo stability of two attenuated auxotrophic mutant strains of Salmonella typhi, 541Ty and 543Ty, as live oral vaccines in humans," J. Clin. Invest. 79(3):888-902.

Littler, et al., 1992, "Human cytomegalovirus UL97 open reading frame encodes a protein that phosphorylates the antiviral nucleoside analogue ganciciovir," Nature 358:160-162.

Low, et al., 1999, "VNP20009, a genetically modified Salmonella Typhimurium for treatment of solid tumors," Proc. Amer. Assoc. for Can. Res. 40:87.

Luo, et al., 1999, "Genetically modified Salmonella typhimurium inhibited growth of primary tumors and metastases," Abstract ZZZ3146. Proc. Amer. Assoc. For Cancer Res. 40:476.

Marr, et al., 1997, "Tumor immunotherapy using an adenoviral vector expressing a membrane-bound mutant of murine TNF alpha," Gene Therapy 4(11):Abstract only;.

Morrison, et al., 1994, "Current Status of Bacterial Endotoxins", AMS News 60:479-484.

Paglia, et al., 1998, "Gene Transfer in Dendritic Cells, Induced by Oral DNA Vaccination With S. Typhimurium, Results in Protective Immunity against a Murine Fibrosarcoma," Blood 92:3172-3176.

Paglia, et al., 2000, "In vivo correction of genetic defects of monocyte/macrophages using attenuated Salmonella as oral vectors for targets gene delivery," Gene Therapy 7:1725-1730.

Saltzman, et al., 1997, "Patterns of hepatic and splenic colonization by an attenuated strain of Salmonella typhimurium containing the gene for human interleukin-2: a novel anti-tumor agent," Cancer Biother. Radiopharm. 12:37-45.

Schacter, 1998, "A Sequential Four-drug Chemotherapy and Biotherapy with Interderon Alpha and GM-CSF-An Innovative Protocol for the Treatment of Metastatic Melanoma," Cancer Biother Radiopharm 13, No. 3: 155-164.

Sznol, 2000, "Use of preferentially replicating bacteria for treatment of cancer," J. Clinical Invest 105:1027-1030.

Tacket, et al., 1997, "Volunteer studies investigating the safety and efficacy of live oral E1 Tor Vibrio cholerae O1 vaccine strain CVD 111," Am J Trop Med Hyg., 56(5):533-537.

Titball and Williamson, 2001, "Vaccination against bubonic and pneumonic plague," Vaccine 19:4175-4184.

Urishima et al., "An Oral CD 40 ligand gene therapy against lymphoma using attenuated Salmonella typhimurium," Blood 95:1258-1263.

Vaara et al., 1999, "Outer membrane permeability barrier in Escherichia coli mutants that are defective in the late acyltransferases of lipid A biosynthesis," J. Bacteriol. 43(6):1459-1462.

Zheng, et al., 2000, "Tumor amplified protein expression therapy: Salmonella as a tumor-selective protein delivery vector," Oncol. Res. 12(3):127-135.

U.S. Appl. No. 09/645,418, filed Aug. 24, 2000, Bermudes et al.

U.S. Appl. No. 11/082,544, filed Mar.17, 2005, Bermudes et al.

International Search Report from the ISA/US for Vion Pharmaceuticals, Inc. et al., International Application No. PCT/US00/23242 (Abandoned Mar. 31, 2006).

PCT International Search Report issued for Vion Pharmaceuticals, Inc., International Application No. PCT/US98/18701 (Abandoned), Filed Sep. 9, 1998, Dated Dec. 21, 1998.

European Communication for Vion Pharmaceuticals, Inc. European Application No. EP 00957764.4, Filed May 3, 2002, Dated Oct. 26, 2006.

Mexican Office Action for Yale University, Mexican App'l No. 979439, Filed Dec. 3, 1997, Dated Jun. 6, 2007.

Lee et al., 2000, "Comparative evaluation of the acute toxic effects in monkeys, pigs, and mice of a genetically engineered Salmonella strain (VNP20009) being developed as an anti-tumor agent," Int. J. of Toxicology 19:19-25.

Sullivan et al., 1992, "A protein kinase homologue controls phosphorylation of ganciclovir in human cytomegalovirus-infected cells," Nature 358:162-164.

U.S. Office Action for King et al., U.S. Appl. No. 10/738,423, Filed Dec. 16, 2003, dated May 18, 2006.

U.S. Office Action for King et al., U.S. Appl. No. 10/738,423, Filed Dec. 16, 2003, dated Jun. 12, 2006.

U.S. Office Action for King et al., U.S. Appl. No. 10/738,423, Filed Dec. 16, 2003, dated Dec. 14, 2006.

U.S. Office Action for King et al., U.S. Appl. No. 10/738,423, Filed Dec. 16, 2003, dated Jun. 28, 2006.

U.S. Advisory Action Before the Filing of an Appeal Brief for King et al., U.S. Appl. No. 10/738,423 Filed Dec. 16, 2003, dated Apr. 5, 2007.

U.S. Notice of Panel Decision from Pre-Appeal Brief Review for King et al., U.S. Appl. No. 10/738,423, Filed Dec. 16, 2003, dated May 18, 2007.

U.S. Office Action for Bermudes et al., U.S. Appl. No. 09/724,390, Filed Nov. 28, 2000, Dated Jun. 17, 2003, (Abandoned).

U.S. Office Action for Bermudes et al., U.S. Appl. No. 09/724,390 (Abandoned), Filed Nov. 28, 2000, Dated Oct. 23, 2002.

U.S. Office Action for Bermudes et al., U.S. Appl. No. 09/724,390 (Abandoned), Filed Nov. 28, 2000, Dated Feb. 12, 2002.

U.S. Office Action for Bermudes et al., U.S. Appl. No. 11/064,533, Filed Feb. 23, 2005, dated Oct. 3, 2006.

U.S. Office Action for Bermudes et al., U.S. Appl. No. 11/064,533, Filed Feb. 23, 2005, dated May 4, 2007.

Notice of Allowance and Fee(s) Due notice for Bermudes et al., U.S. Appl. No. 11/064,533, Filed Feb. 23, 2005, dated Aug. 1, 2007.

U.S. Office Action for Pawelek et al., U.S. Appl. No. 08/486,422 (Abandoned), Filed Jun. 7, 1995, Dated Aug. 5, 1997.

U.S. Office Action for Pawelek et al., U.S. Appl. No. 08/486,422 (Abandoned), Filed Jun. 7, 1995, Dated Apr. 15, 1997.

U.S. Office Action for Pawelek et al., U.S. Appl. No. 10/723,570 (Abandoned), Filed Nov. 24, 2003, Dated Dec. 6, 2006.

U.S. Office Action for Pawelek et al., U.S. Appl. No. 10/723,570 (Abandoned), Filed Nov. 24, 2003, Dated Aug. 9, 2005.

U.S. Office Action for Bermudes et al., U.S. Appl. No. 11/082, 544, Filed Mar. 17, 2005, Dated Oct. 21, 2005.

U.S. Office Action for Bermudes et al., U.S. Appl. No. 11/082, 544, Filed Mar. 17, 2005, Dated Dec. 23, 2005.

U.S. Office Action for Bermudes et al., U.S. Appl. No. 11/082, 544, Filed Mar. 17, 2005, Dated Sep. 27, 2005.

U.S. Advisory Action for Bermudes et al., U.S. Appl. No. 11/082, 544, Filed Mar. 17, 2005, Dated Dec. 11, 2006.

U.S. Office Action for Bermudes et al., U.S. Appl. No. 10/187,278, Filed Jun. 27, 2002, Dated Mar. 23, 2004.

U.S. Office Action for Bermudes et al., U.S. Appl. No. 10/187,278, Filed Jun. 27, 2002, Dated Aug. 25, 2004.U.

Notice of Allowance and Fee(s) Due for Bermudes et al., U.S. Appl. No. 10/187,278, Filed Jun. 27, 2002, Dated Oct. 20, 2004.

U.S. Office Action for Bermudes et al., U.S. Appl. No. 10/125,328, Filed Apr. 18, 2002, Dated Mar. 24, 2004.

U.S. Office Action for Bermudes et al., U.S. Appl. No. 10/125,328, Filed Apr. 18, 2002, Dated Aug. 25, 2004.

Notice of Allowance and Fee(s) Due for Bermudes et al., U. S. Appl. No. 10/125,328, Filed Apr. 18, 2002, Dated Sep. 22, 2004

U.S. Office Action for King et al., U.S. Appl. No. 10/738,423, Filed Dec. 16, 2003, dated Jul. 11, 2006.

European Communication for Vion Pharmaceuticals, Inc., European App'l No.98946891.3, Filed Sep. 9, 1998, Dated Apr. 10, 2007.

European Communication issued on Apr. 10, 2007 for Vion Pharmaceuticals, Inc., European App'l No. EP 98946891.3

Levine, et al., "Safety, infectivity, immunogenicity, and in vivo stability of two attenuated auxotrophic mutant strains of *Salmonella typhi* 541Ty and 543Ty, as live oral vaccines in humans," J. Clin. Invest. 79(3):888-902.

U.S. Office Action for Bermudes et al., U.S. Appl. No. 11/082,544, Filed Mar. 17, 2005, Dated Dec. 12, 2007.

Notice of Allowance and Fee(s) Due notice for Bermudes et al., U.S. Appl. No. 11/064,533, Filed Feb. 23, 2005, Dated Nov. 15, 2007.

U.S. Office Action for Bermudes et al., U.S. Appl. No. 10/738,423, Filed Feb. 16, 2003, Dated Dec. 20, 2007.

Chinese Office Action for Vion Pharmaceuticals, Inc., Chines Application No. 00816714.1, Filed Aug. 24, 2000, Dated Jun. 4, 2004.

Chinese Decision on Rejection for Vion Pharmaceuticals, Inc., Chinese Application No. 00816714.1, Filed Aug. 24, 2000, Dated Apr. 7, 2006.
Israeli Office Action for Vion Pharmaceuticals, Inc., Israeli Application No. 134936, Filed Jul. 3, 2000, Dated Dec. 24, 2007.
Mexican Office Action for Vion Pharmaceuticals, Inc., Mexican Application No. 2000/002355, Filed Mar. 8, 2000, Dated Sep. 18, 2007.
Mexican Office Action for Vion Pharmaceuticals, Inc., Mexican Application No. 979439, Filed Dec. 3, 1997, Dated Jul. 27, 2007.
Mexican Office Action for Vion Pharmaceuticals, Inc., Mexican Application No. 979439, Filed Dec. 3, 1997, Dated May 2, 2005.
Mexican Office Action for Vion Pharmaceuticals, Inc., Mexican Application No. 979439, Filed Dec. 3, 1997, Dated May 30, 2007.
Mexican Office Action for Vion Pharmaceuticals, Inc., Mexican Application No. 979439, Filed Dec. 3, 1997, Dated Jan. 20, 2006.
U.S. Office Action for Bermudes et al., U.S. Appl. No. 09/645,415, now Patent No. 6,962,969, Filed Aug. 24, 2000, Dated May 28, 2002.
U.S. Office Action for Bermudes et al., U.S. Appl. No. 09/645,415, now Patent No. 6,962,696, Filed Aug. 24, 2000, Dated Nov. 19, 2002.
U.S. Office Action for Bermudes et al., U.S. Appl. No. 09/645,415, now Patent No. 6,962,696, Filed Aug. 24, 2000, Dated May 15, 2003.
U.S. Office Action for Bermudes et al., U.S. Appl. No. 09/645,415, now Patent No. 6,962,696, Filed Aug. 24, 2000, Dated Feb. 23, 2004.
U.S. Office Action for Bermudes et al., U.S. Appl. No. 09/645,415, now Patent No. 6,962,696, Filed Aug. 24, 2000, Dated Sep. 9, 2004.
U.S. Advisory Action for Bermudes et al., U.S. Appl. No. 09/645,415, now Patent No. 6,962,696, Filed Aug. 24, 2000, Dated Dec. 3, 2004.
U.S. Notice of Allowance for Bermudes et al., U.S. Appl. No. 09/645,415, now Patent No. 6,962,696, Filed Aug. 24, 2000, Dated Jan. 11, 2005.
U.S. Office Action for Pawelek et al,. U.S. Appl. No. 08/486,422, Filed Jun 7, 1995, Dated Aug. 5, 1997.
U.S. Office Action for Pawelek et al., U.S. Appl. No. 09/358,052, Filed Jul. 21, 1999, Dated Apr. 10, 2000.
U.S. Office Action for Pawelek et al., U.S. Appl. No. 09/358,052, filed Jul. 21, 1999, Dated Nov. 17, 2000.
U.S. Office Action for Pawelek et al., U.S. Appl. No. 09/358,052, filed Jul. 21, 1999, Dated Dec. 18, 2002.
U.S. Office Action for Pawelek et al., U.S. Appl. No. 09/358,052, filed Jul. 21, 1999, Dated Jun. 3, 2003.
U.S. Office Action for Pawelek et al., U.S. Appl. No. 08/658,034, filed Jun. 4, 1996, Dated Feb. 5, 1997.
U.S. Office Action for Pawelek et al., U.S. Appl. No. 08/658,034, filed Jun. 4, 1996, Dated Oct. 24, 1997.
U.S. Office Action for Pawelek et al., U.S. Appl. No. 08/658,034, filed Jun. 4, 1996, Dated Jul. 7, 1998.
U.S. Office Action for Pawelek et al., U.S. Appl. No. 08/658,034, filed Jun. 4, 1996, Dated Jan. 21, 1999.
U.S. Office Action for Pawelek et al., U.S. Appl. No. 08/658,034, filed Jun. 4, 1996, Dated Aug. 4, 1999.
U.S. Notice of Allowance for Bermudes et al., U.S. Appl. No. 09/337,689, filed Jun. 22, 1999, Dated Dec. 15, 2000.
U.S. Notice of Allowance for Bermudes et al., U.S. Appl. No. 09/337,689, filed Jun. 22, 1999, Dated Feb. 27, 2001.
U.S. Notice of Allowance for Bermudes et al., U.S. Appl. No. 09/337,689, filed Jun. 22, 1999, Dated Oct. 9, 2001.
U.S. Notice of Allowance for Bermudes et al., U.S. Appl. No. 09/337,689, filed Jun. 22, 1996, Dated Mar. 8, 2002.
U.S. Office Action for Bermudes et al., U.S. Appl. No. 09/149,832, filed Sep. 8, 1998, Dated Mar. 27, 2000.
U.S. Supplemental Office Action for Bermudes et al., U.S. Appl. No. 09/149,832, filed Sep. 8, 1998, Dated Apr. 6, 2000.
U.S. Office Action for Bermudes et al., U.S. Appl. No. 09/149,832, filed Sep. 8, 1998, Dated Sep. 11, 2000.
U.S. Office Action for Bermudes et al., U.S. Appl. No. 09/149,832, filed Sep. 8, 1998, Dated May 1, 2001.
U.S. Office Action for Bermudes et al., U.S. Appl. No. 09/149,832, filed Sep. 8, 1998, Dated Nov. 20, 2001.
U.S. Notice of Allowance for Bermudes et al., U.S. Appl. No. 09/149,832, filed Sep. 8, 1998, Dated Mar. 15, 2002.
U.S. Supplemental Notice of Allowance for Bermudes et al., U.S. Appl. No. 09/149,832, filed Sep. 8, 1998, Dated Apr. 19, 2002.
U.S. Office Action for Pawelek et al., U.S. Appl. No. 10/723,570, filed Nov. 24, 2003, Dated Apr. 11, 2006.
U.S. Office Action for Bermudes et al., U.S. Appl. No. 089/926,636, Now Patent No. 6,080,849, filed Sep. 10, 1998, Dated Apr. 29, 1998.
U.S. Notice of Allowance for Bermudes et al., U.S. Appl. No. 08/926,636, Now Patent No. 6,080,849, filed Sep. 10, 1997, Dated Feb. 3, 1999.
U.S. Supplemental Notice of Allowance for Bermudes et al., U.S. Appl. No. 08/926,636, Now Patent No. 6,080,849, filed Sep. 10, 1997, Dated Mar. 15, 1999.
Japanese Office Action for Yale University, Japanese Application No. 09-502263, filed Dec. 8, 1997, Dated Feb. 5, 2002.
Japanese Office Action for Yale University, Japanese Application No. 09-502263, filed Dec. 8, 1997, Dated Apr. 30, 2003.
Australian Examiner's Report for Vion Pharmaceuticals, Inc., Australian Application No. 69334/00, filed Apr. 9, 2002, Dated Nov. 1, 2004.
Australian Examiner's Report for Vion Pharmaceuticals, Inc., Australian Application No. 69334/00, filed Apr. 9, 2002, Dated Jun. 27, 2005.
Australian Examiner's Report for Vion Pharmaceuticals, Inc., Australian Application No. 69334/00, filed Apr. 9, 2002, Dated Oct. 21, 2005.
Australian Examiner's Report for Yale University, Australian Application No. 63851/96, filed Dec. 5, 1997, Dated Nov. 3, 1999.
Australian Examiner's Report for Yale University, Australian Application No. 63851/96, filed Dec. 5, 1997, Dated Oct. 26, 1998.
Australian Notice of Acceptance for Yale University, Australian Application No. 63851/96, filed Dec. 5, 1997, Dated Mar. 23, 2000.
Australian Examiner's Report for Vion Pharmaceuticals, Inc., Australian Application No. 93807/98, filed Mar. 8, 2000, Dated May 1, 2001.
Australian Examiner's Report for Vion Pharmaceuticals, Inc., Australian Application No. 93807/98, filed Mar. 8, 2000, Dated Apr. 19, 2002.
Australian Notice of Acceptance for Vion Pharmaceuticals, Inc., Australian Application No. 93807/98, filed Mar. 8, 2000, Dated May 24, 2002.
Brazilian Written Opinion for Yale University, Brazilian Application No. PI 9609016-2, filed Dec. 8, 1997, Dated Jun. 27, 2006.
Brazilian Written Opinion for Yale University, Brazilian Application No. PI 9609016-2, filed Dec. 8, 1997, Dated Sep. 11, 2007.
Chinese Office Action for Yale University, Chinese Application No. 96196140.6, filed Jun. 5, 1996, Dated Jul. 28, 2002.
Chinese Office Action for Yale University, Chinese Application No. 96196140.6, filed Jun. 5, 1996, Dated Apr. 11, 2003.
Chinese Office Action for Vion Pharmaceuticals, Inc., Chinese Application No. 98811030.X, now Patent No. ZL99811020.X, filed Sep. 9, 1998, Dated Feb. 20, 2004.
European Communication for Vion Pharmaceuticals, Inc., European Application No. 00957765.4, filed May 3, 2002, Dated Aug. 22, 2007.
European Communication for Yale University, European Application no. 96923299.0, filed Jun. 6, 1996, Dated Nov. 19, 2003.
European Communication for Yale University, European Application No. 96923299.0, filed Jun. 6, 1996, Dated Jul. 23, 2004.
European Communication for Vion Pharmaceuticals, Inc., European Application No. 98946891.3, filed Sep. 9, 1998, Dated Dec. 6, 2004.
European Search Report for Vion Pharmaceuticals, Inc., European Application No. 98946891.3, filed Sep. 9, 1998, Dated Sep. 1, 2004.
European Communication for Vion Pharmaceuticals, Inc., European Application No. 98946891.3, filed Sep. 9, 1998, Dated Apr. 10, 2007.
European Search Report for Vion Pharmaceuticals, Inc., European Application No. 98946891.3, filed Sep. 9, 1998, Dated May 13, 2005.
Israeli Office Action for Vion Pharmaceuticals, Inc., Israeli Application No. 148933, filed Mar. 27, 2002, Dated Jan. 16, 2007.
Israeli Office Action for Vion Pharmaceuticals, Inc., Israeli Application No. 148933, filed Mar. 27, 2002, Dated Jun. 27, 2007.
Israeli Office Action for Vion Pharmaceuticals, Inc., Israeli Application No. 134936, filed Jul. 3, 2000, Dated Jan. 8, 2006.
Korean Notice of Decision to Grant for Yale University, Korean Application No. 10-1997-0709128, filed Dec. 8, 1997, Dated Feb. 13, 2004.

Korean Office Action for Vion Pharmaceuticals, Inc., Korean Application No. 2000-7002535, filed Mar. 10, 2000, Dated Feb. 3, 2005.
Mexican Office Action for Vion Pharmaceuticals, Inc., Mexican Application No. PA/2002/003384, filed Apr. 3, 2002, Dated Feb. 3, 2006.
Mexican Office Action for Vion Pharmaceuticals, Inc., Mexican Application No. PA/2000/002355, filed Mar. 8, 2000, Dated Sep. 8, 2003.
New Zealand Office Action for Vion Pharmaceuticals, Inc., New Zealand Application No. 518354, filed Apr. 12, 2002, Dated Aug. 14, 2003.
New Zealand Office Action for Vion Pharmaceuticals, Inc., New Zealand Application No. 518354, filed Apr. 12, 2002, Dated Nov. 26, 2004.
New Zealand Notice of Acceptance for Vion Pharmaceuticals, Inc., New Zealand Application No. 518354, filed Apr. 12, 2002, Dated Feb. 11, 2005.
New Zealand Examiner's Report for Yale University, New Zealand Application No. 312341, filed Dec. 10, 1997, Dated Jul. 24, 1998.
New Zealand Examiner's Report for Yale University, New Zealand Application No. 312341, filed Dec. 10, 1997, Dated Mar. 3, 1999.
New Zealand Notice of Acceptance for Yale University, New Zealand Application No. 312341, filed Dec. 10, 1997, Dated Apr. 26, 1999.
New Zealand Examiner's Report for Vion Pharmaceuticals, Inc., et al., New Zealand Application No. 503376, filed Mar. 14, 2000, Dated Nov. 9, 2000.
New Zealand Notice of Acceptance for Vion Pharmaceuticals, Inc., et al., New Zealand Application No. 503376, filed Mar. 14, 2000, Dated Oct. 3, 2002.
Chinese Office Action for Vion Pharmaceuticals, Inc., Chinese Application No. 00816714.1, filed Aug. 24, 2000, Dated Jun. 4, 2004.
Chinese Office Action for Vion Pharmaceuticals, Inc., Chinese Application No. 00816714.1, filed Aug. 24, 2000, Dated Mar. 4, 2005.
Chinese Decision on Rejection for Vion Pharmaceuticals, Inc., Chinese Application No. 00816714.1, filed Aug. 24, 2000, Dated Apr. 7, 2006.
International Search Report from the ISA/US for Vion Pharmaceuticals, Inc., International Applicatoin No. PCT/US00/23242, filed Aug. 3, 2000, Dated Apr. 12, 2001.
International Preliminary Examination Report from the IPEA/US for Vion Pharmaceuticals, Inc., International Application No. PCT/US00/23242, filed Aug. 4, 2000, Dated Dec. 3, 2002.
International Search Report from the ISA/US for Vion Pharmaceuticals, Inc,. International Application No. PCT/US98/18701, filed Sep. 9, 1998, Dated Dec. 21,1998.
International Search Report from the ISA/US for Vion Pharmaceuticals, Inc., International Application No. PCT/US96/10250, filed Jun. 5, 1996, Dated Sep. 10, 1996.
Adler, 1973, "A Method for Measuring Chemotaxis and Use of the Method to Determine Optimum Conditions for Chemotaxix by *Escherichia coli*," J. Gen. Microbiol. 74:77-91.
Alizadeh, et al., 1994, "Apoptosis as a Mechanism of Cytolysis of Tumor Cells by a Pathogenic Free-Living Amoeba," Infect. Immun. 62:1298-1303.
Anderson, W.F., 2001, "Recombinant DNA Advisory Committee Meeting, Jun. 14-15, 2001: Protocols Reviewed," Human Gene Therapy, 12:1593-1595.
Anderson, et al., 1996, "Development of attenuated Salmonella strains that express heterologous antigens," Methods in Molecular Medicine: Vaccine protocols, ed. A. Robinson, G. Farrar, C. Wiblin, Humana Press, New Jersey, pp. 47-62.
Bagshawe, 1995, "Antibody-Directed Enzyme Prodrug Therapy: A Review," Drug Dev. Res. 34:220-230.
Barry, et al., 1995, "Protection Against Mycoplasma Infection Using Expression-Library Immunization," Nature 377:632-635.
Barth and Morton, 1995, "The Role of Adjuvant Therapy in Melanoma Management," Cancer 75 (Suppl.):726-734.
Berggren, 1995, "Recombinant Salmonella as an Oral HIV Vaccine," NIH Project No. 5 08 AI01248-02.
Bone, 1993, "Gram-Negative Sepsis: A Dilemma of Modern Medicine," Clin. Microbiol. Rev. 6:57-68.

Bonneoh, et al., 1995, "Inhibition of Melanoma Growth by Adenoviral-Mediated HSV Thymidine Kinase Gene Transfer in vivo," J. Invest. Derm. 104:313-317.
Carey, et al., "Clostridial Oncolysis in Man," Eur. J. Cancer 3:37-46.
Carrier, et al., 1992, "Expression of Human IL-1 beta in Salmonella typhimurium; a Model System for the Delivery of Recombinant Therapeutic Protiens in vivo," J. Immunol. 148:1176-1181.
Carswell, et al., 1975, "An Endotoxin-Induced Serum Factor that Causes Necrosis of Tumors," Proc. Natl. Acad. Sci. USA 72:3666-3670.
Chabolgoity, et al., 1996, "A *Salmonella typhimurium* htrA Live Vaccine Expressing Multiple Copies of a Peptide Comprising Amino Acids 8-23 of Herpes Simplex Virus Glycoprotein D as a Genetic Fusion to Tetanus Toxin Fragment C Protects Mice frmo Herpes Simplex Virus Infection," Mol. Microbiol. 19:791-801.
Christ, et al,. 1995, "E5531, a Pure Endotoxin Antagonist of High Potency," Science 268:80-83.
Clements, 1995, "Attenuated Salmonella as Vaccine Vectors," NIH Project No. 5 RO1 AI 28835-06.
Clementz, et al., 1997, "Function of the Escherichia coil msbB Gene, a Multicopy Suppressor of htrB Knockouts, in the Acylation of Lipid A," J. Biol. Chem. 272(16):10353-10360.
Cunningham, et al., 1992, "Actin-Binding Protein Requirement for Cortical Stability and Efficient Locomotion," Science 255:325-327.
Cunningham, C. and Neumanaitis, J., 2001, "Recombinant DNA Advisory Committee Meeting, Jun. 14-15, 2001: Protocols Reviewed," Human Gene Therapy 12:1594-1596.
Curtiss, 1995, "Biological Containment of Live Bacterial Vaccines," NIH Project No. 1 R41 AI38599-01.
Curtiss, 1994, "Avirulent Salmonella Host-Vector Vaccine Systems," NIH Project No. 1 R41 AI36585-01.
Eisenstadt, 1987, "Analysis of Mutagenesis," from *Escherichia coli* and *Salmonella typhimurium* , Cellular and Molecular Biology, Neidhardt, et al. (ed.), pp. 1016-1033.
Eisenstein, et al., 1995, "Immunotherapy of a Plasmacytoma with Attenuated Salmonella," Med. Oncol. 12:103-108.
Engel, et al., 1992, "Murein-metabolizing enzymes from *Escherichia coil*: existence of a second lytic transglycosylase," J. Bacteriol. 174:6394-6403.
Engelbert and Gericke, 1963, "Oncolysis by Clostridia. v. Transplanted Tumors of the Hamster," Cancer Res. 24:239-243.
Falkow, 1991, "Bacterial Entry into Euaryotic Cells," Cell 65:1099-1102.
Fields, et al., 1989, "A Salmonella locus that controls resistance to microbial proteins from phagocytic cells," Science 243:1059-1062.
Fields, et al., 1986, "Mutants of *Salmonella typhimurium* that cannot survive within themacrophage are avirulent," Proc. Natl. Acad. Sci. USA, 83:5189-5193.
Fox, et al., 1996, "Anaerobic Bacteria as a Delivery System for Cancer Gene Therapy: in vitro Activation of 5-Fluorocystine by Genetically Engineered Clostridia," Gene Therapy 3:173-178.
Friberg, 1993, "BCG in the Treatment of Superficial Cancer of the Bladder: A Review," Med. Oncol. Tumor Pharmacother. 10:31-36.
Galan, 1995, "Novel Salmonella Antigen Delivery Vectors," NIH Project No. 5 RO1 AI36520-02.
Gericke and Engelbart, 1963, "Oncolysis by Clostridia. II. Experiments on a Tumor Spectrum with a Variety of Clostridia in Combination with Heavy Metal," Cancer Res. 24:217-221.
Gulig, 1994, "*Salmonella typhimurium* Virulence Plasmid," NIH Project No. 5 R29 AI28421-05.
Hall, et al., 1994, "Induced Regression of Bovine Papillomas by Intralesional Immunotherapy," Therapeutic Immunol. 1:319-324.
Han, et al., 1967, "Salmonellois in Disseminated Malignant Diseases," New Eng. J. Med. 276:1045-1052.
Hoiseth and Stocker, 1981, "Aromatic dependent *Salmonella typhimurium* are non virulent and effective as live vaccines," Nature 291:238-239.
Jain, 1994, "Barriers to Drug Delivery in Solid Tumors," Sci. American 271:58-65.
Jones, et al., 1992, "Invasion by *Salmonella typhymurium* is Affected by the Direction of Flagellar Rotation," Infect. Immun. 60:2475-2780.

Karow and Georgopoulos, 1992, "Isolation and Characterization of the *Escherichia coli* msbB Gene, a Multicopy Suppressor of Null Mutations in the High-Temperature Requirement Gene htrB," J. Bactériol. 174:702-710.

Kelley, et al., 1993, "The firA gene of *E. coli* encodes UDP-3-O-(R-3-hydroxymyristoyl)-glucosamine—acetyltransferase," J. Biol. Chem. 268:19866-19874.

Khan, et al., 1998, "A Lethal Role for Lipid A in Salmonella Infections," Molecular Microbiology, 29(3):571-579, XP002292668.

King, et al., 1998, "Tumor targeted Salmonella expressing cytosine deaminase converted 5-fluorocytosine to 5-fluorouricil and inhibited tumor growth in vivo," Proc. Of the Amer. Assoc. for Can. Res. 39:512.

Klimpel, et al., 1990, "Bacteria-Infected Fibroblasts have Enhanced Susceptibility to the Cytotoxic Action of Tumor Necrosis Factor," J. Immunol. 145:711-717.

Lee, et al., 1992, "Identification of a *Salmonella typhimurium* Invasion Locus by Selection for Hyperinvasive Mutants," Proc. Natl. Acad. Sci. USA 89:1847-1851.

Lemmon, et al., 1997, "Anaerobic Bacteria as a Gene Delivery System that is Controlled by the Tumor Microenvironment," Gene Therapy, 4:79-796.

Lemmon, et al., 1994, "Anaerobic Bacteria as a Gene Delivery System to Tumors," Proc. Am. Assn. Cancer Res. 35:374. (Abstract 2231).

Levine, 1995, "Recombinant and Live Oral *Salmonella typhi* Vaccines," NIH Project No. 5 RO1 AI29471-06.

Lindgren, et al., 1996, "Macrophage killing is an essential virulence mechanism of *Salmonella typhimurium*," PNAS 93(9):4197-4201.

Low, et al., 1999, "Lipid A mutant Salmonella with suppressed virulence and TNFa induction retain tumor-targeting in vivo," Nature Biotechnology, 17:37-41.

Low, et al., 1998, "Disruption of the Salmonella msbB Gene Suppresses Virulence and TNFalph Induction yet Retains Tumor-Targeting in Vivo," Proceedings of the American Association for Cancer Research Annual Meeting, 39:60, XP001182904.

Loppnow, et al., 1990, "Cytokine induction by Lipopolysaccharide (LPS) Corresponds to Lethal Toxicity and is Inhibited by Nontoxic Rhodobacter capsulatus LPS," Infect. Immun. 58:3743-3750.

Lytvyn, at al., 1992, "Comparison of the Thymidine Kinase Genes from Three Entomopoxviruses," J. Gen. Virol. 73:3235-3240.

MacEwen, et al., 2001, "Genetically Modified Salmonella for Canine Cancer: A Phase I Study," Annual Meeting of the American College of Veterinary Internal Medicine, Abstract 82.

Macnab, 1992, "Genetics and Biogenesis of Bacterial Flagella," Ann. Rev. Genet. 26:131-158.

Mahan, et al., 1993, "Selection of Bacterial Virulence Genes that are Specifically Induced in Host Tissues," Science 259:686-688.

McLaughlin, et al., 1979, "Synergistic Activity of Components of Mycobacteria and Mutant Salmonella in Causing Regression of Line-10 Tumors in Guinea Pigs," Cancer Res. 39:1766:1771.

Michalek, 1994, "Genetically Engineered Oral Vaccines and Caries Immunity," Abstract, NIH Project No. 5 R01 DE09081-05.

Mier, et al., 2001, "Phase I Trial of a Live, Attenuated *Salmonella typhimurium* (VNP20009) Administered by Direct Intro-Tumoral Injection," Proc. Am. Soc. Clin. Oncol. 20:29.

Miller, 1995, "Entry into Eukaryotic Cells by Salmonella and Yersinia, " NIH Project Number 5 K04 AI01230-02.

Miller, et al., 1992, "An Unusual pagC: TnphoA Mutation Leads to an Invasion and Virulence-Defective Phenotype in Salmonellae," Infect. Immun. 60:3763-3770.

Miller, et al., 1989, "A Two-Component Regulatory System (phoP phoQ) Controls *Salmonella typhimurium* Virulence," Proc. Natl. Acad. Sci. USA 86:5054-5058.

Minton, et al., 1995, "Chemotherapeutic Tumor Targeting Using Clostridial Spores," FEMS Micro. Rev. 17:357-364.

Möse and Möse, 1963, "Oncolysis by Clostridia. I. Activity of Clostridium butyricum (M-55) and Other Nonpathenogenic Clostridia Against the Erhlich Carcinoma," Cancer Res. 24:212-216.

Mullen, et al., 1992, "Transfer of the Bacterial Gene for Cytosine Deaminase to Mammalian Cells Confers Lethal Sensitivity to 5-Fluorocytosine: A Negative Selection System," Proc. Natl. Acad. Sci. USA 89:33-37.

Nauts, et al., 1953, "A Review of the Influence of Bacterial Infection and of Bacterial Products (Coley's Toxins) on Malignant Tumors in Man," Acta Medica Scandanavica 145 (Suppl. 276):1-105.

O'Callaghan, et al., 1988, "Characterization of aromatic and purine dependent *Salmonella typhimurium*: Attenuation, persistence, and ability to induce protective immunity in BALB/c mice," Infect. And Immun. 56:419-423.

Pan, et al., 1995, "A Recombinant Listeria monocytogenes Vaccine Expressing a Model Tumor Antigen Protects Mice Against Lethal Tumor Cell Challenge and Causes Regression of Established Tumors." Nature Medicine 1:471-477.

Parker, et al., 1947, "Effect of Histolyticus Infection and Toxin on Transplantable Mouse Tumors," Proc. Soc. Exp. Biol. Med. 16124:461-467.

Pawelek, et al., 1997, "Tumor-targeted Salmonella as a Novel Anticancer Vector," Cancer Res. 57:4537-4544.

Pawelek, et al., 1996, "Tumor-targeted Salmonella as a Novel Antimelanoma Vector," Melanoma Research, 4th World Conference on Melanoma, Sydney, Australia, Jun. 10-14, 1996, vol. 7, (Suppl. 1), S141. Abstract.

Pawelek, et al., 1995, "Macrophage Characteristics of Metastatic Melanoma," J. Invest. Dermatol. 104:605 (Abstract 304).

Pidherney, et al., 1993, "In vitro and in vivo Tumoricidal Properties of a Pathogenic Free-Living Amoeba," Cancer Letters 72:91-98.

Pugsley, 1988, "Protein Secretion Across the Outer Membrane of Gram-Negative Bacteria," Protein Transfer and Organell Biogenesis, D. and Robbins, (eds.), Academic Press, Inc. Harcourt Brace Jovanovich, Publishers, San Diego, pp. 607-652.

Raue and Cashel, 1975, "Regulation of RNA Synthesis in *Escherichia coli*," Biochemica et Biophysica Acta 383:290-304.

Reinhard, et al., 1950, "Chemotherapy of Malignant Neoplastic Diseases," JAMA 142:383-390.

Saltzman, et al., 1996, "Attenuated Salmonella typhimurium Containing Interleukin-2 Decreases MC-38 Hepatic Metastases: a Novel Anti-Tumor Agent," Cancer Biotherapy and Radiopharmaceuticals 11:145-153.

Schaer, et al., 1992, "Induction of a Cellular Immune Response to a Foreign Antigen by a Recombinant Listeria monocytogenes Vaccine," J. Immunol. 149:53-59.

Schlechte and Elbe, 1988, "Recombinant Plasmid DNA Variation of Clostridium oncolyticum-Model Experiments of Cancerostatic Gene Transfer," Zbl. Bakt. Hyg. A 268:347-356.

Schlechte, et al., 1982, "Chemotherapy for Tumours Using Clostridial Oncolysis, Antibiotics and Cyclophosphamide: Model Trial on the UVT 15264 Tumor," Arch. Geschwulstforsch. 52:41-48.

Shaw, et al., 1991, "The Human Dioxin-Inducible NAD(P)H: Quinone Oxidoreductase cDNA-Encoded Protein Expressed in COS-1 Cells is Identical to Diaphorase 4," Eur. J. Biochem. 195:171-176.

Sizemore, et al., 1997, "Interaction of *Salmonella typhi* strains with cultured human monocyte-derived macrophages," Infect. Immunity 65:309-312.

Sizemore, et al., 1995, "Attenuated Shigella as a DNA Delivery Vehicle for DNA-Mediated Immunization," Science 270:299-302.

Slauch, et al., 1994, "In vivo Expression Technology for Selection of Bacterial Genes Specifically Induced in Host Tissues," Meth. Enzymol. 235:481-492.

Somerville, et al., 1996, "A Novel Escherichia Coli Lipid, a Mutant That Produces an Anti-inflammatory Lipopolysaccharide," Journal of Clinical Investigation, 97(2):359-365, XP002910255.

Sosnowski, et al., 1994, "Complications of Bacillus Calmette-Guerin (BCG) Immunotherapy in Superficial Bladder Cancer," Comp. Ther. 20:695-701.

Sternberg and Maurer, 1991, "Bacteriophage mediated generalized transduction in *Escherichia coli* and *Salmonella typhimurium*," Methods in Enzymology 204:18-43.

Su, et al., 1992, "Extracellular Export of Shiga Toxin B-Subunit/ Haemolysin A (C-terminus) Fusion Protein Expressed in *Salmonella typhimurium* aroA-Mutant and Stimulation of B-Subunit Specific Antibody Responses in Mice," Microbial Pathogenesis, 13:465-476.

Sunshine, et al., 1997, "Mutation of the htrB Gene in Virulent *Salmonella typhimurium* Strain by Intergeneric Transduction: Strain Construction and Phenotype Characterization," J. Bacteriol. 179(17):5521-5533.

Tacket CO, 2000, "Phase 2 clinical trial of attenuated *Salmonella enterica serovar typhi* oral live vector vaccine CVD 908-htrA in U.S. volunteers," Infect. Immun. 68(3):1196-1201.

Tacket CO, 1997, "Safety of live oral *Salmonella typhi* vaccine strains with deletions in htrA and aroC aroD and immune response in humans," Infect. Immun. 65(2):452-456.

Tacket CO, 1992, "Comparison of the safety and immunogenicity of delta aroC delta aroD and delta cya delta crp *Salmonella typhi* strains in adult volunteers," Infect. Immun. 60(2):536-541.

Takayama, et al., 1989, "Diphosphoryl Lipid A from *Rhodopseudomonas sphaeroides* ATCC 17023 Blocks Induction of Cachectin in Macrophages by Lipopolysaccharide," Infect. Immun. 57:1336-1338.

Theile, et al., 1963, "Oncolysis by Clostridia. III. Effects of Clostridia and Chemotherapeutic Agents on Rodent Tumors," Cancer Res. 24:222-232.

Thiele, et al., 1963, "Oncolysis by Clostridia. IV. Effect of Nonpathogenic Clostridial Spores in Normal and Pathological Tissues," Cancer Res. 24:234-238.

Toso, et al., 2002, "Phase 1 Study of the Intravenous Administration of Attenuated Salmonella Typhimurium to Patients with Metastatic Melanoma," J. of Clin. Oncol. 20:142-152.

Tuomanen, 1993, "Subversion of Leuocyte Adhesion Systems by Respiratory Pathogens," Am. Soc. Microbiol. 59:292-296.

Vinopal, 1987, "Selectable Phenotypes," *Escherichia coli* and *Salmonella typhimurium*, Cellular and Molecular Biology, Neidhardt, et al., (ed.), pp. 990-1015.

Wolfe, et al., 1971, "Salmonellosis in Patients with Neoplastic Disease," Arch. Intern. Med. 128:547-554.

Zheng, et al., 1997, "Attenuated *Salmonella typhimurium* inhibited tumor metastasis in vivo," Proc. Amer. Assoc. Can. Res. 38:9.

U.S. Appl. No. 11/627,743, filed Jan. 26, 2007, King, et al.

Supplemental Partial European Search Report for Vion Pharmaceuticals, Inc. European App'l No. 00957764.1, filed May 3, 2002, Dated Oct. 10, 2005.

European Search Report issued on May 13, 2005 for Vion Pharmaceuticals, Inc., European App'l No. EP 98946891.3.

Aranda, et al., 1992, "*Salmonella Typhiurium* activates virulence gene transcription within acidified macrophage phagosomes," Proc. Natl. Acad. Sci USA 89:10079-10083.

Bacon, et al., 1950, "The effects of biochemical mutation on the virulence of Bacterium Typhosum: the induction and isolation of mutants," Br. J. Exp. Path. 31:703-713.

Bacon, et al., 1950, "The effects of biochemical mutation on the virulence of Bacterium Typhosum: the virulence of mutants," Br. J. Exp. Path. 31:714-724.

Bacon, et al., 1951, "The effects of biochemical mutation on the virulence of Bacterium Typhosum: the loss of virulence of certain mutants," Br. J. Exp. Path. 32:85-96.

Bast et al., 1975, "Antitumor activity of bacterial infection. I. Effect of Listeria monocytogenes on growth of a murine fibrosarcoma, II. Effect of Listeria monocytogenes on growth of a guinea pig hepatoma" J Natl Cancer Inst. 54(3):749-761.

Bisno, et al., 1990 Classification of Streptococci, Principles and Practice of Infectious Diseases, 1518-1519.

Cowan, et al., 1974, "Part 8-Gram-Negative Facultative Anaerobic Rods," Determinative Biology, 8th ed., 290-340.

Gupta, et al., 1995, "A Potent Inhibitor of Endothelial Cell Proliferation is Generated by Proteolytic Cleavage of the Chemokine Platelet Factor 4," Proc. Natl. Acad. Sci USA 92:7799-7803.

Hibbs, et al., 1976, "Role of activated macrophages in nonspecific resistance to neoplasia," J Reticuloendithel Soc 20:223-231.

Hohmann, et al., 1995, "Macrophage-inducible expression of a model antigen in *Salmonella typhimurium* enhances immunogenicity," Proc Natl Acad Sci U S A 92:2904-8.

Hunter et al., "Cutting edge: systemic inhibition of angiogenesis underlies resistance to tumors during acute toxoplasmosis," J Immunol 166:5878-81.

Iruela-Arispe, et al., 1999, "Inhibition of Angiogensis by Thrombospondin-1 is Mediated by 2 Independent Regions Within the Type 1 Repeats," Am. Hear Assoc 100:1423-1431.

Keller et al., 1990, "Resistance to a non-immunogenic tumor, induced by *Corynebacterium parvum* or Listeria monocytogenes, is abrogated by anti-interferon gamma," Int J Cancer 46:687-90.

Koshimura, 1961, "On the streptolysin S synthetizing and anticancer activities of cell-free extract from living hemolytic streptococci," Cancer Chemother Rep. 13:107-111.

Lee, et al., "Identification of a *Salmonella typhimurium* Invasion Locus by Selection for Hyperinvasive Mutants", Proc. Nta. Acad. Sci. USA, 89:1847-1851.

Mizutani, et al., 1980, "Inhibitory effect of some intestinal bacteria on liver tumorigenesis in gnotobiotic C3H/He male mice," Cancer Letters 11:89-96.

Mullen et al., 1994, " Tumors expressing the cytosine deaminase suicide gene can be eliminated in vivo with 5-fluorocytosine and induce protective immunity to wild type tumor," Cancer Res 54:1503-1506.

Murata et al., 1965, "Oncolytic effect of *Proteus mirabilis* upon tumor bearing animal," Life Sci 4(10):1055-67.

North, et al., 1977, "T-cell-mediated concomitant immunity to syngeneic tumors. I. Activated macrophages as the expressors of nonspecific immunity to unrelated tumors and bacterial parasites," J Exp Med 145(2):275-292.

Okamoto, et al., 2002, "Enhancement of anti-tumor immunity by lipoteichoic acid-related molecule isolated from OK-432, a streptococcal agent, in athymic nude mice bearing human salivary adenocarcinoma: role of natural killer cells," Anticancer Res. 22(6A):3229-39.

Okuno, et al., 1990, "Immunomodulating effect of intratumoral (IT) injection of biological response modifiers (BRM) on tumor-bearing hosts," J. Jpn Soc Cancer Ther 25(8):1543-1549. (abstract only).

Raetz, et al., 1993 "Bacterial endotoxins: extraordinary lipids that activate eucaryotic signal transduction," J. Bacteriol. 175(18):5745-53.

Reilly, et al., 1953, "Microbiology and cancer therapy; review," Cancer Res. 13(12):821.

Romick, et al., 1996, "Aerobic and Anaerobic Metabolism of Listeria monocytogenes in Defined Glucose Medium," Applied and Environmental Microbiol 304-307.

Roy, et al., "Mutations in firA, encoding the second scyltransferase in lipopolysachiride biosynthesis, affect multiple steps in lipopolysacchiride biosynthesis," J Bacteriol. 176(6):1639-46.

Sakamoto, et al., 1988 Antitumor effect of normal intestinal microflora on Erlich ascites tumor Jpn. J. Cancer Res. 79:109-116.

Simonen, et al., 1993, "Protein secretion in Bacillus species," Microbiological Revews 57(1);109-137.

Tsujitani, 1998 "Endoscopic intratumoral injection of OK-432 and Langerhans' in patients with gastric carcinoma," Cancer 61(9):1749-53.

Youdim, et al., 1977, "Cooperation of immune lymphoid and reticuloendothelial cells during Listeria monocytogenes-mediated tumor immunity," Cancer Res 37(4):991-996.

Youdim, et al., 1976, Resistance to tumor growth mediated by Listeria monocytogenes. Destruction of experimental malignant melanoma by LM-activated peritoneal and lymphoid cells. J Immunol. 116(3):579-584.

Youdim, et al., 1976, "Resistance to tumor growth mediated by Listeria monocytogenes: collaborative and suppressive macrophage-lymphocyte interactions in vitro," J Immunol 117(5 Pt.2):1860-5.

Youdim, et al., 1974, "Nonspecific Suppression of Tumor Growth by an Immune Reaction to Listeria Monocytogenes," J Natl Cancer Inst 52(1):193-198.

Cunningham, et al., 2001, "A phase I trial of genetically modified *Salmonella typhimurium* expressing cytosine deaminase (TAPET-CD, VNP20029) administered by intratumoral injection in combination with 5-fluorocytosine for patient with advanced metastatic cancer" Human Gene Ther., 12: 1594-1596.

Dunstan, et al., 1999, "Use of in vivo-regulated promoters to deliver antigens from attenuated *Salmonella enterica* var. Typhimurium" Infect. Immun., 67(10):5133-41.

Elkins, et al., 1994, "In vivo delivery of interleukin-4 by a recombinant vaccinia virus prevents tumor development in mice," Human Gene Ther., 5(7);809-820.

Low, et al., 1998, "Disruption of the Salmonella msbB gene suppresses virulence and TNF-alpha induction yet retains tumor-targeting in vivo", Proc. Amer. Assoc. Cancer Res Annual Meeting, 39: 60 (abst 409).

Zinkernagel, et al., 1974 "Early appearance of sensitized lymphocytes in mice infected with Listeria monocytogenes", J Immunol, 112(2):496-501.

Clairmont, et al., 2000, Biodistribution and genetic stability of the novel antitumor agent VNP 200009, a genetically modified strain of Salmonella typhimurium, J. Infect. Diseases, 181:1996-2002.

Nemunaitis, et al., 2003, "Pilot trial of genetically modified, attenuated Salmonella expressing the *E. coli* cytosine deaminase gene in refractory cancer patients," Cancer Gene Ther 10:737-44.

Pascual, et al., 1997, "Oral Bacterial Vaccine Vectors for the Delivery of Subunit and Nucleic Acid Vaccines to the Organized Lymphoid Tissue of the Intestine," Behring Inst. Mitt. 98:143-152.

Somerville, et al., 1999, "*Escherichia coli* msbB Gene as a Virulence Factor and a Therapeutic Target," Infect And Immunity 67(12):6583-6590.

Sternberg, et al., 1991, "Bacteriophage-mediated Generalized Transduction in *Escherichia coli* and *Salmonella typhimurium*" Methods in Enzymology, 204: 18-43.

Yu, et al., 2004, "Visualization of tumors and metastases in live animals with bacteria and vaccinia virus encoding light-emitting proteins" Nat Biotechnol. Mar. 2004; 22(3):313-20.

Platt, et al., 2000, "Anti-tumor effects of genetically engineered Salmonella in combination with radiation," Eur. J. Cancer 36: 2397-2402.

Altmann, et al., 1995, "Expression and Purification of a Synthetic Human Obese Gene Product,", Protein Expression and Purification, vol. 6:722-726.

European Communication for Vion Pharmaceuticals, Inc., European App'l No. 00 957 764.4, filed Dec. 3, 1997, Dated Mar. 5, 2008.

Jirillo, et al., 1986, "Relationship between Immune System and Gram-Negative Bacteria. Acid-Treated Salmonella Minnesota R595(Re) Enhances Immune Responsiveness in Patients With Gynecologic Malignancies," International Journal of Immunopharmcology, vol. 8(8):881-886.

PCT Written Opinion for Vion Pharmaceuticals, Inc., International Application No. PCT/US1998/018701, filed Sep. 9, 1998, Dated Oct. 28, 1999.

PCT International Preliminary Report for Vion Pharmaceuticals, Inc., International Application No. PCT/US1998/018701, filed Sep. 9, 1998, Dated Apr. 9, 1999.

Brazilian Office Action for Vion Pharmaceuticals, Inc., Brazilian Application No., filed Mar. 10, 2000, Dated Feb. 12, 2008.

European Office Action for Vion Pharmaceuticals, Inc., European Application No. 98 946 891.3, filed Sep. 9, 1998, Dated Mar. 19, 2008.

Israeli Office Action for Vion Pharmaceuticals, Inc., Israeli Application No. 148933, filed Mar. 27, 2002, Dated Mar. 31, 2008.

Israeli Office Action for Vion Pharmaceuticals, Inc., Israeli Application No. 148933, filed Mar. 27, 2002, Dated Mar. 31, 2008.

Japanese Office Action for Vion Pharmaceuticals, Inc., Japanese Application No. 2000-510842, filed Mar. 10, 2000, Dated May 20, 2008.

Mexican Notice of Allowance for Vion Pharmaceuticals and Yale University, Mexican App'l No. 2000002355, filed Mar. 8, 2000, Dated Feb. 12, 2008.

Singapore Notification of Grant for Vion Pharmaceuticals, Inc., Singapore App'l No. 200201817-4, filed Aug. 24, 2000, Dated Sep. 30, 2005.

Belcourt, M. F. et al., "Expression of the mitomycin C activating enzyme DT-diaphorase in tumor-target Salmonella", Proceedings of the American Association for Cancer Research Annual, Mar. 2000, No. 41, p. 466 Abstract #2972, 91st Annual Meeting of the American Association for Cancer Research, San Francisco, California USA, Apr. 01-05, 2000.

Bochner, B. et al., Aug. 1980, "Positive Selection for Loss of Tetracycline Resistance", Journal of Bacteriology, vol. 143(2):926-933.

Clairmont, C. et al., "Enhanced Antitumor Activity from Tumor-Targeting Salmonella Expressing Endostatin," Vion Pharmaceuticals, Inc., Poster Presentation from 91st Annual Meeting of the American Association for Cancer Research, San Francisco, California USA, Apr. 01-05, 2000.

Clairmont, C. et al., "Enhanced Antitumor Activity from Tumor-Targeting Salmonella Expressing Endostatin," Proceedings of the American Association for Cancer Research Annual, Mar. 2000, No. 41, p. 732 Abstract #4653, 91st Annual Meeting of the American Association for Cancer Research, San Francisco, California.

Clairmont, C. et al., "Expression of colcin E3 by tumor-targeted Salmonella", Proceedings of the American Association for Cancer Research Annual, Mar. 2000, No. 41, p. 466 Abstract #2971, 91st Annual Meeting of the American Association for Cancer Research, San Francisco, California USA, Apr. 01-05, 2000.

Coley, William B., Jan. 1991, "The Treatment of Malignant Tumors by Repeated Inoculations of Erysipelas with a Report of Ten Original Cases," Clinical Orthopaedics and Related Research, vol. 262:3-11. Abridged from Coley, W.B.: The treatment of malignant tumors by repeated inoculations of erysipelas: With a report of ten original cases. Am. J. Med. Sci. vol. 105;487:1983.

Donnenberg, M.S. and Kaper, J.B., Dec. 1991. "Construction of an eae Deletion Mutant of Enteropathic *Escherichia coli* by Using a Positive Selection Suicide Vector," Infection and Immunity, vol. 59(12):4310-4317.

Elsinghorst, Eric, 1994, "Measurement of Invasion by Gentamycin Resistance," Methods in Enzymology, vol. 236:405-420.

Elsinghorst, E. and Weitz, J., Aug. 1994, "Epithelial cell invasion and Adherence Directed by the Enterotoxigenic *Escherichia coli* tib Locus is Associated with a 104-Kilodalton Outer Membrane Protein," Infection and Immunity, vol. 62(8): 3463-3471.

Enard, W. et al., Apr. 12, 2002, "Intra- and Interspecific Variation in Primate Gene Expression Patterns," Science, vol. 296:340.

Fonstein, M. et al., Apr. 1994, "Tn10-Mediated Invasions Fuse Uridine Phosphorylase (udp) and rRNA Genes of Eschrichia coli," Journal of Bacteriology, vol. 176(8):2265-2271.

Grillot-Courvalin et al., 2002, "Wild-Type Intracellular Bacteria Deliver DNA into Mammalian Cells", Cellular Microbiology, vol. 4(3):117-186.

Helin, H., 1986. "Macrophage procoagulant factors-mediators of inflammatory and neoplastic tissue lesions," Med. Biol. vol. 64(4): 167-76. [Abstract only].

Karsten, V. et al., "A strain of *Salmonella typhimurium* VNP20009 expressing an anti-angiogenic peptide from platelet factor-4 has enhanced anti-tumor activity", Proceedings of the American Association for Cancer Research Annual, Mar. 2001, No. 41, p. 687, Abstract #3700.

King et al., Jul. 1, 2002, "Tumor-targeted Salmonella Expressing Cytosine Deaminase as an Anticancer Agent", Human Gene Therapy, vol. 13:1225-1233.

King, I. et al., "Tumor-selective delivery of therapeutic proteins by *Salmonella typhimurium* in murine tumor models", Proceedings of the American Association for Cancer Research Annual, Mar. 2000, No. 41, p. 732, Abstract #4652, 91st Annual Meeting of the American Association for Cancer Research, San Francisco, California USA, Apr. 01-05, 2000.

Kurashige et al., 1983, "Synergistic anti-tumor effect of mini-cells prepared from *Salmonella typhimurium* with mitomycin C in EL4-bearing mice," Cancer Immunol. Immunother. vol. 14(3):202-4. [Abstract only].

Li, Z., et al., "Tissue distribution and in vivo expression of cytosine deaminase by TAPET-CD, a genetically engineered strain of *Salmonella typhimurium* as an anti-tumor vector", Proceedings of the American Association for Cancer Research Annual, Mar. 2001, No. 41, p.687, Abstract #3699.

Low et al,. Nov. 4, 2003, "Construction of VNP20009: A Novel Genetically Stable Antibiotic-Sensitive Strain of Tumor-Targeting Salmonella for Parenteral Administration in Humans", Methods in Molecular Medicine, vol. 90:47-59.

Luo et al., 2001, "Antitumor Effect of VNP20009, an Attenuated Salmonella, in Murine Tumor Models", Oncology Research, vol. 12:501-508.

Luo, X. et al., "Intra-tumoral administration of VNP20009 targeted and inhibited distal uninjected tumors and lung metastases", Proceedings of the American Association for Cancer Research, San Francisco, California USA, Apr. 01-05, 2000.

Muday, G.K. and Hermann, K.M., May 1990, "Regulation of the *Salmonella typhimurium* aroF gene in Escherichia coli,"Journal of Bacteriology, vol. 172(5):2259-2266.

Murray et al., May 2001, "Growth Defects in msbB-Salmonella can be Suppressed by an Extragenic Loss-of-Function Mutation", 101 General Meeting of the American Society for Microbiology: Abstracts, p. 138-139.

Pasqualini, R. et al., Jun. 1997, "αv integrins as receptors for tumor-targeting by circulating ligands," Nature Biotechnology, vol. 15:542-546.

Preface from *Escherichia coli* and Salmonella, Cellular and Molecular Biology, Second Edition, vol. 1, Ed. Frederick C. Neidhardt, 1996.

Sauter B.V. et al., Apr. 25, 2000, "Adenovirus-mediated gene transfer of endostatin in vivo results in high level of transgene expression and inhibition of tumor growth and metastases," PNAS, vol. 97(9):4802-4807.

Smith, C.D. et al., Feb. 1975, "Improved Culture Method for the Isolation of Histoplasma capsulatum and Blastomyces dermatitidus from Contaminated Specimens," A.J.C.P (American Journal of Clinical Pathology). vol. 63:276-280.

Taylor-Robinson, David, 1990, "Ureaplasma Urealyticum (T-Strain Mycoplasma) and Mycoplasma Hominis," Chapter 163 of Ureaplasma Urealyticum and Mycoplasma Hominis, 1458-1463.

Urashima et al., Feb. 2000, "An Oral CD40 Ligand Gene Therapy Against Lymphoma Using Attenuated *Salmonella typhimurium*", Blood, Vol. vol. 95(4):1258-1263.

Van der Wal, F.J. et al., Feb. 1998, "Optimization of Bacteriocin Release Protein (BRP)-Mediated Protein Release by *Escherichia coli*: Random Mutagenesis of the pCloDF13-Derived BRP Gene to Uncouple Lethality and Quasi-Lysis from Protein Release," Applied and Environmental Microbiol. vol. 64(2):392.

Van der Wal, F.J. et al., Dec. 1995, "Bacteriocin release proteins: mode of action, structure, and biotechnological application," FEMS Microbiology Review, vol. 17(4): 381-399.

Vercesi, A.E. et al,. Nov. 20, 1998, "Respiration and Oxidative Phosphorylation in the Apicomplexan Parasite Toxoplasma gondii,"The Journal of Biological Chemistry, vol. 273(47):31040-31047.

Vickerman, Keith, 1990, "*Phylum zoomastigina* Class Kinetoplastida," Handbook of Protocista, 215-238.

Vivier, Emille and Desportes, Isabelle, 1990, "Phylum Apicomplexa," Handbook of Protocista, 549-573.

Wu, S.S. and Kaiser, D., Oct. 1996, "Markerless Deletions of pil Genes in Myxococcus Xanthus generated by Counterselection with the Bacillus subtilis sacB Gene." Journal of Bacteriology, vol. 178 (19):5817-5821.

Yuhua et al., 2001, "Oral Cytokine Gene Therapy Against Murine Tumor Using Attenuated *Salmonella typhimurium*," International Journal of Cancer, vol. 94:438-443.

Bochner et al., Aug. 1980, "Positive Selection for Loss of Tetracycline Resistance", Journal of Bacteriology, vol. 143(2): 926-933.

Critchley at al., 2004, "Potential Therapeutic Applications of Recombinant, Invasive *E. coli*", Gene Therapy, vol. 11: 1224-1233.

Darveau, Richard, Jan. 1999, "Infection, Inflammation, and Cancer", Nature Biotechnology, vol. 17:19-19.

Pawelek et al., published online Jul. 1996, "*Salmonella typhimurium* as a Therapeutic Vectos for Melanoma", Pigment Cell Research, vol. 9(5): p. 49.

U.S. Final Office Action for Pawelek et al., U.S. Appl. No. 08/846,422, filed Jun. 7, 1995, Dated May 12, 1998.

Notice of Allowance and Fee(s) Due notice for Bermudes et al., U.S. Appl. No. 11/082,544, filed Mar. 17, 2005, Dated Jul. 10, 2008.

Chinese Notice of Reexamination for Vion Pharmaceuticals, Inc., Chinese App'l No. 00816714.1, filed Aug. 24, 2000, Dated Jul. 29, 2008.

```
GATCAACCAGCAAGCCGTTAACCCTCTGACAGCAAAATTGCCGCGAAGGTCTGACGGGGTCAGATGGTCGTGAATACCTGGCACA    90

GGTGAAGAGGTTCTGCCGCAACTGGCCTTCGATTAACAAATGGCTGACAGACCCGTACGGCATGTGTGCCGGCTTTTTGTTTGTG   180

M  E  T  K  K  N  N  S  E
TGAGACGCAGAGTCGCTACACTATTCACAATTCCTTTTCCGTCAGCAGAGCATGGAAACCAAAAAAAATAATAGTGAG           270

Y  I  P  E  F  E  K  S  F  R  Y  P  Q  Y  W  G  A  W  L  G  A  A  A  M  A  G  I  A  L  T
TATATCCCTGAATTCGAAAAATCCTTTCGCTATCCACAGTATTGGGGCGCCTGGTTGGGGGCGGCCATGGCGGGGATCGCATTAACA  360

P  A  S  F  R  D  P  L  L  A  T  L  G  R  F  A  G  R  L  G  K  S  S  R  R  A  L  I  N
CCGGCATCATTCCGGCGACCCTTTGCTGCGACGGCGTTTGCCGGACGGCTGGGGAAGAGTTCTCGTCGCCGGCGCTAATTAAT     450

L  S  L  C  F  P  Q  R  S  E  A  E  R  E  A  I  V  D  E  M  F  A  T  A  P  Q  A  M  A  M
CTGTCGTTGTGTCCGCAGCGTAGCGAAGCTGAGCGCGAAGCTGATTGTCGCCACCGCGCCACAGGCAATGGCGGATG            540

M  A  E  L  A  M  R  G  P  K  K  I  Q  Q  R  V  D  W  E  G  L  E  I  I  E  E  M  R  R  N
ATGGCTGAGTTGGCGATGCGCGGTCCGAAAAAAATTCAACACGCGTGTTGACTGGGAAGGTCTGGAGATTATCGAGGAGATGCGTAAC 630

D  E  K  V  I  F  L  V  P  H  G  W  G  V  D  I  P  A  M  L  M  A  S  Q  G  Q  K  M  A  A
GACGAAAAAGTCATTTTTCTCGTCCCGCATGGCTGGGGCGTCGACATTCCAGCCATGCTGATGGCCTCTCAGGGGCAAAAAATGGCGGCG 720

M  F  H  N  Q  G  N  P  V  F  D  Y  I  W  N  T  V  R  R  R  F  G  G  R  L  H  A  R  N  D
ATGTTTCATAATCAGGGTAATCCGGTTTTTGACTATATCTGGAACACAGTGCGTCGGCGGTTTGGCGGGACGTTTGCATGCGTAATGAC 810

G  I  K  P  F  I  Q  S  V  R  Q  G  Y  W  G  Y  Y  L  P  D  D  H  G  P  E  H  S  E  F
GGGATTAAACCCTTTATTCAGTCTGTTCGTCAGGGCTACTGGGGTTACTACCTGCCCGACCAGGATCACGGCCCGAGCATAGTGAATTC 900
```

FIG.1A

```
V  D  F  F  A  T  Y  K  A  T  L  P  A  I  G  R  L  M  K  V  C  R  A  R  V  I  P  L  F  P
GTTGATTCTTTGCCGACATACAAAGCGACGCTGCCTGCAATTGGTCGGCTGATGAAAGTGTGCCGCGACGGTGATACCGGCTTTCCCG        990

V  Y  N  G  K  T  H  R  L  T  I  Q  I  R  P  P  M  D  D  L  L  T  A  D  D  H  T  I  A  R
GTGTATAATGCTAAAACCCATCGCCTGACTATCCAGATTCGCCCGCCAATGGACGATCTGCTCACGGCTGACGACCACACTATCGCCAGA      1080

R  M  N  E  E  V  E  I  F  V  G  P  H  P  E  Q  Y  T  W  I  L  K  L  L  K  T  R  K  P  G
CGGATGAACGAAGAGGTCGAAATTTTTGTCGGCCCGCATCCGGAACAGTACACCTGGATCCTGAAGCTGCTCAAAACCCGCAAGCCAGGC     1170

E  I  Q  P  Y  K  R  K  D  L  Y  P  I  K
GAGATTCAGCCGTATAAGCGTAAAGATCTTTATCCCATCAAATAAATAAAGCCTCTCGTAAGAGAGCTTTATGCTGACAAACCCTGTAC      1260

TACCTGATGAACACGGCGTGGGGCAGTTTTTACTTCAACGCGTCAAAATACGCTGTATTGGTTGAACGACGTGCTCATGACATCGCCCTG    1350

GGTCACCGATAACCAGGTCGCCGGAAACCAGATACCCTTTATCGCCCAGCAGATTAACAGCTTCATGTGCCGACAACGCCATCAGCCCC     1440

GCTATCAAAATGCACCGGCGTTACTCCGCGATAGAGCGCGGTCAGGTTCAGCGTGCCGTTGATGGGCGGACATCGCGTAACGCCTTTCAGTGGTTTGCCGCATA 1530

GGACCTGATACGGGAAGTCATTAGCCGCGATTCGTCATGGTGATGATCGCGTACCACGGGCTGTTTAGACACATTGATGCTGGGGATTTTTTCTGC      1620

CATGCCAGACAGACGGCGCCAATGGCGTTCTTCAACGTCTTGTCAACTGCACGTCGAGACGGTGTTTAGACACATTGATGCTGGGGATTTTTTCTGC     1710

GCCCAGGCAGACGCGGCCATTGCGCACGGGCTGCGGCATGCGGTTTCGGCAGACGATAACTGACGGCTCGGCCATCGGGTTGGTGATCATGACTCCGTGCC 1800

ATCCAGGACGGCGTTCGCCACGTCCACTTCCCGCACGGTCGCCATGGGTCGCCATCGGGTTGGTGATCATGACTCCATCATTTGCGTTGCGGTGAT      1890

GACTGCCGCGTTTAGCTGACGCGCACGGCGAATCAGCGCCTTTCTGATACCAACCAGCTCGGATCGCCGATTCAACGCCCAGATCGCC            1980

ACGTGCCACCATCACAACGTCAGAGGCCAGAATGATATC                                                             2019
```

FIG.1B

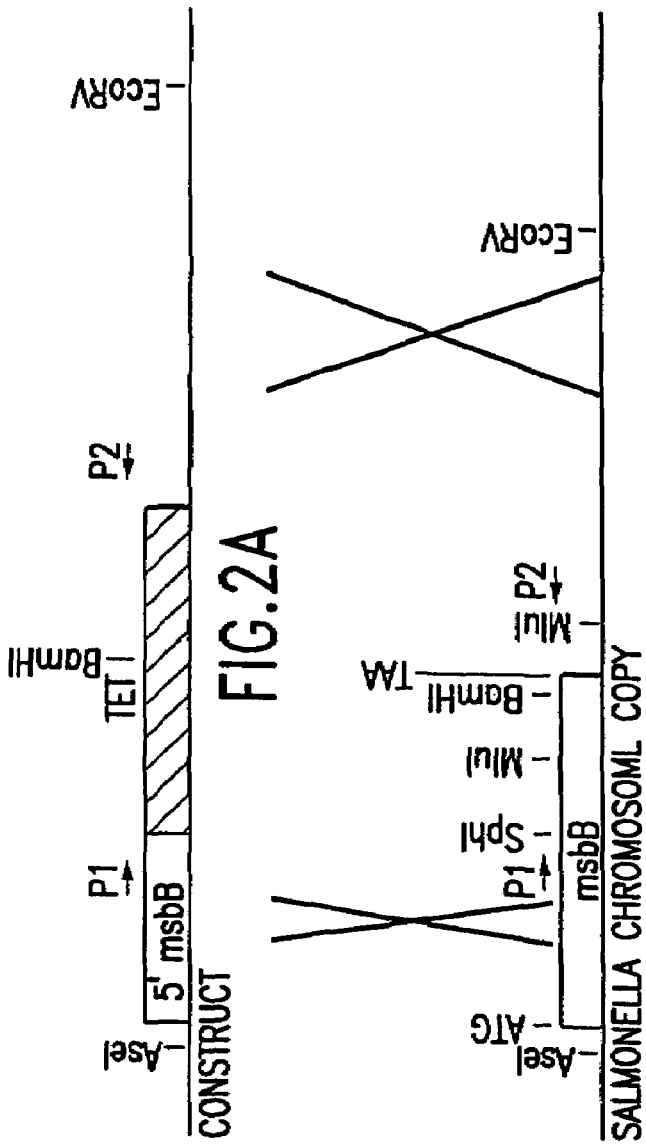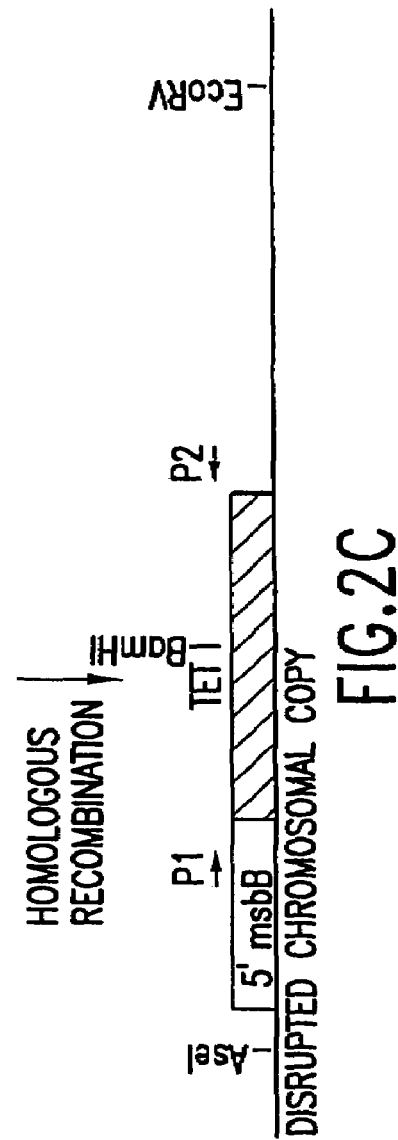

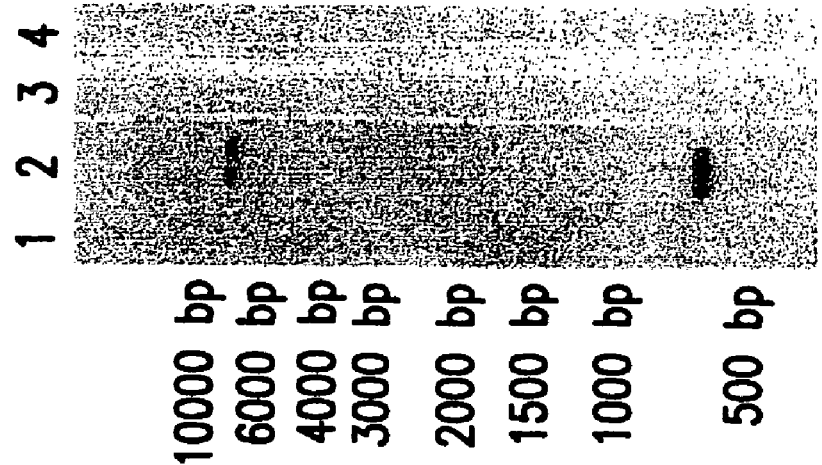
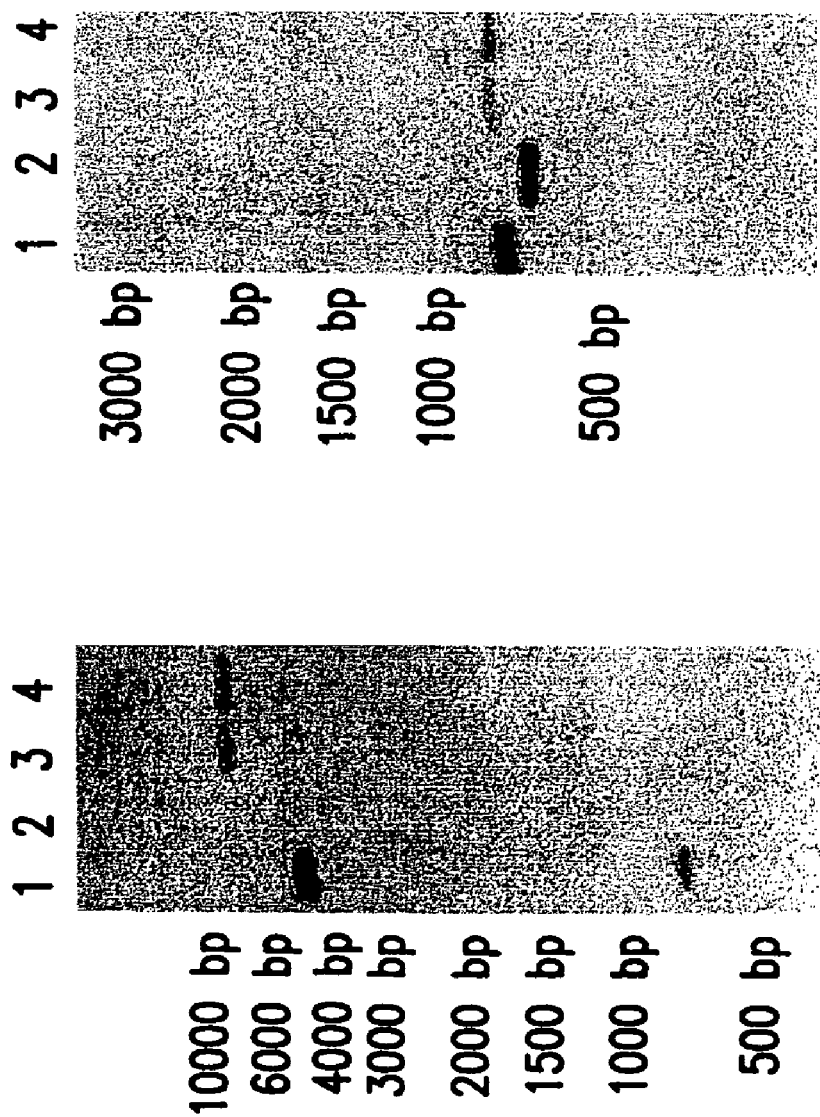
FIG. 3A  FIG. 3B  FIG. 3C

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 2019 base pairs
      (B) TYPE: nucleic acid
      (C) STRANDEDNESS: single (D) TOPOLOGY: linear (ii) MOLECULE TYPE: DNA (ix) FEATURE:
   (A) NAME/KEY: Coding Sequence
   (B) LOCATION: 244...1210
   (D) OTHER INFORMATION:

(xi) SEQUENCE DESCRIPTION: SEQ ID NO: 1:

```
GATCAACCAG CAAGCCGTTA ACCCTCTGAC AGCAAAATTG CCGCGCACGG AAGGTCTGAC      60

GGGGTCAGAT CGTCGTGAAT ACCTGGCACA GGTGAAAGAG GTTCTGCCGC AACTGCGCTT     120

CGATTAACAA ATGCGCTGAC AGAGCCGGTA CGCGATGTGT GCCGGCTTTT TTGTTTTGTG     180

TGAGACGCAG ACGTCGCTAC ACTATTCACA ATTCCTTTTC GCGTCAGCAG ACCCTGGAAA     240

AGC ATG GAA ACC AAA AAA AAT AAT AGT GAG TAT ATC CCT GAA TTC GAA       288
    Met Glu Thr Lys Lys Asn Asn Ser Glu Tyr Ile Pro Glu Phe Glu
    1               5                  10                  15

AAA TCC TTT CGC TAT CCA CAG TAT TGG GGC GCC TGG TTG GGC GCG GCG       336
Lys Ser Phe Arg Tyr Pro Gln Tyr Trp Gly Ala Trp Leu Gly Ala Ala
                20                  25                  30

GCA ATG GCG GGG ATC GCA TTA ACA CCG GCA TCA TTC CGC GAC CCT TTG       384
Ala Met Ala Gly Ile Ala Leu Thr Pro Ala Ser Phe Arg Asp Pro Leu
            35                  40                  45

CTG GCG ACG CTG GGG CGT TTT GCC GGA CGG CTG GGG AAG AGT TCT CGT       432
Leu Ala Thr Leu Gly Arg Phe Ala Gly Arg Leu Gly Lys Ser Ser Arg
        50                  55                  60

CGC CGG GCG CTA ATT AAT CTG TCG TTG TGC TTT CCG CAG CGT AGC GAA       480
Arg Arg Ala Leu Ile Asn Leu Ser Leu Cys Phe Pro Gln Arg Ser Glu
    65                  70                  75

GCT GAG CGC GAA GCG ATT GTC GAT GAG ATG TTC GCC ACC GCG CCA CAG       528
Ala Glu Arg Glu Ala Ile Val Asp Glu Met Phe Ala Thr Ala Pro Gln
80                  85                  90                  95

GCA ATG GCG ATG ATG GCT GAG TTG GCG ATG CGC GGT CCG AAA AAA ATT       576
Ala Met Ala Met Met Ala Glu Leu Ala Met Arg Gly Pro Lys Lys Ile
                100                 105                 110

CAA CAG CGT GTT GAC TGG GAA GGT CTG GAG ATT ATC GAG GAG ATG CGT       624
Gln Gln Arg Val Asp Trp Glu Gly Leu Glu Ile Ile Glu Glu Met Arg
            115                 120                 125

CGT AAC GAC GAA AAA GTC ATT TTT CTC GTA CCG CAT GGC TGG GGC GTC       672
Arg Asn Asp Glu Lys Val Ile Phe Leu Val Pro His Gly Trp Gly Val
        130                 135                 140

GAC ATT CCA GCC ATG CTG ATG GCC TCT CAG GGG CAA AAA ATG GCG GCG       720
Asp Ile Pro Ala Met Leu Met Ala Ser Gln Gly Gln Lys Met Ala Ala
    145                 150                 155

ATG TTT CAT AAT CAG GGT AAT CCG GTT TTT GAC TAT ATC TGG AAC ACA       768
Met Phe His Asn Gln Gly Asn Pro Val Phe Asp Tyr Ile Trp Asn Thr
160                 165                 170                 175

GTG CGT CGG CGT TTC GGC GGA CGT TTG CAT GCG CGT AAT GAC GGG ATT       816
Val Arg Arg Arg Phe Gly Gly Arg Leu His Ala Arg Asn Asp Gly Ile
                180                 185                 190

AAA CCC TTT ATT CAG TCT GTT CGT CAG GGC TAC TGG GGT TAC TAC CTG       864
Lys Pro Phe Ile Gln Ser Val Arg Gln Gly Tyr Trp Gly Tyr Tyr Leu
            195                 200                 205

CCG GAC CAG GAT CAC GGC CCG GAG CAT AGT GAA TTC GTT GAT TTC TTT       912
Pro Asp Gln Asp His Gly Pro Glu His Ser Glu Phe Val Asp Phe Phe
        210                 215                 220

GCG ACA TAC AAA GCG ACG CTG CCT GCA ATT GGT CGG CTG ATG AAA GTG       960
Ala Thr Tyr Lys Ala Thr Leu Pro Ala Ile Gly Arg Leu Met Lys Val
    225                 230                 235
```

-continued

```
TGC CGC GCA CGC GTG ATA CCG CTT TTC CCG GTG TAT AAT GGT AAA ACG      1008
Cys Arg Ala Arg Val Ile Pro Leu Phe Pro Val Tyr Asn Gly Lys Thr
240                 245                 250                 255

CAT CGC CTG ACT ATC CAG ATT CGC CCG CCA ATG GAC GAT CTG CTC ACG      1056
His Arg Leu Thr Ile Gln Ile Arg Pro Pro Met Asp Asp Leu Leu Thr
                260                 265                 270

GCT GAC GAC CAC ACT ATC GCC AGA CGG ATG AAC GAA GAG GTC GAA ATT      1104
Ala Asp Asp His Thr Ile Ala Arg Arg Met Asn Glu Glu Val Glu Ile
            275                 280                 285

TTT GTC GGC CCG CAT CCG GAA CAG TAC ACC TGG ATC CTG AAG CTG CTC      1152
Phe Val Gly Pro His Pro Glu Gln Tyr Thr Trp Ile Leu Lys Leu Leu
        290                 295                 300

AAA ACC CGC AAG CCA GGC GAG ATT CAG CCG TAT AAG CGT AAA GAT CTT      1200
Lys Thr Arg Lys Pro Gly Glu Ile Gln Pro Tyr Lys Arg Lys Asp Leu
    305                 310                 315

TAT CCC ATC A AATAAATAAA GCCTCTCGTA AGAGAGGCTT TATGCTGACA AACCCTG    1257
Tyr Pro Ile Lys
320

TACTACCTGA TGAACAGGCG TGGGGGAGTT TTACTCAACG GTCAAAATAC GCGTGGTATT   1317
GGTTGAACCG ACGGTGCTCA TGACATCGCC CTGGGTCACG ATAACCAGGT CGCCGGAAAC   1377
CAGATACCCT TTATCGCGCA GCAGATTAAC AGCTTCATGT GCCGCGACAA CGCCATCAGC   1437
CGCGCTATCA AATGCACCG GCGTTACTCC GCGATAGAGC GCGGTCAGGT TCAGCGTGCG    1497
TTCATGGCGC GACATGGCGA AAATCGGCAG GCCGGAGCTG ATACGGGAAG TCATTAGCGC   1557
GGTACGACCG GATTCCGTCA TGGTGATGAT CGCGGTAACG CCTTTCAGAT GGTTTGCCGC   1617
ATACACTGCA GACATGGCAA TGGCTTCTTC AACGTTGTCG AACTGCACGT CGAGACGGTG   1677
TTTAGACACA TTGATGCTGG GGATTTTTTC TGCGCCCAGG CACACGCGCG CCATTGCGGC   1737
AACGGTTTCA GAAGGATACT GACCGGCTGC GGTTTCGGCA GACAGCATAA CCGCATCCGT   1797
GCCATCCAGG ACGGCGTTCG CCACGTCCAT CACTTCCGCA CGGGTCGGCA TCGGGTTGGT   1857
GATCATCGAC TCCATCATTT GCGTTGCGGT GATGACTGCG CGGTTTAGCT GACGCGCACG   1917
GCGAATCAGC GCTTTCTGGA TACCAACCAG CTCCGGATCG CCGATTTCAA CGCCCAGATC   1977
GCCACGTGCG ACCATCACAA CGTCAGAGGC CAGAATGATA TC                     2019
```

(2) INFORMATION FOR SEQ ID NO: 2:

(i) SEQUENCE CHARACTERISTICS:
        (A) LENGTH: 323 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 2:

```
Met Glu Thr Lys Lys Asn Asn Ser Glu Tyr Ile Pro Glu Phe Glu Lys
1               5                   10                  15

Ser Phe Arg Tyr Pro Gln Tyr Trp Gly Ala Trp Leu Gly Ala Ala Ala
            20                  25                  30

Met Ala Gly Ile Ala Leu Thr Pro Ala Ser Phe Arg Asp Pro Leu Leu
        35                  40                  45

Ala Thr Leu Gly Arg Phe Ala Gly Arg Leu Gly Lys Ser Ser Arg Arg
    50                  55                  60

Arg Ala Leu Ile Asn Leu Ser Leu Cys Phe Pro Gln Arg Ser Glu Ala
65                  70                  75                  80

Glu Arg Glu Ala Ile Val Asp Glu Met Phe Ala Thr Ala Pro Gln Ala
```

```
                85                  90                  95
Met Ala Met Met Ala Glu Leu Ala Met Arg Gly Pro Lys Lys Ile Gln
            100                 105                 110
Gln Arg Val Asp Trp Glu Gly Leu Glu Ile Ile Glu Glu Met Arg Arg
            115                 120                 125
Asn Asp Glu Lys Val Ile Phe Leu Val Pro His Gly Trp Gly Val Asp
            130                 135                 140
Ile Pro Ala Met Leu Met Ala Ser Gln Gly Gln Lys Met Ala Ala Met
145                 150                 155                 160
Phe His Asn Gln Gly Asn Pro Val Phe Asp Tyr Ile Trp Asn Thr Val
                165                 170                 175
Arg Arg Arg Phe Gly Gly Arg Leu His Ala Arg Asn Asp Gly Ile Lys
                180                 185                 190
Pro Phe Ile Gln Ser Val Arg Gln Gly Tyr Trp Gly Tyr Tyr Leu Pro
                195                 200                 205
Asp Gln Asp His Gly Pro Glu His Ser Glu Phe Val Asp Phe Phe Ala
                210                 215                 220
Thr Tyr Lys Ala Thr Leu Pro Ala Ile Gly Arg Leu Met Lys Val Cys
225                 230                 235                 240
Arg Ala Arg Val Ile Pro Leu Phe Pro Val Tyr Asn Gly Lys Thr His
                245                 250                 255
Arg Leu Thr Ile Gln Ile Arg Pro Pro Met Asp Asp Leu Leu Thr Ala
                260                 265                 270
Asp Asp His Thr Ile Ala Arg Arg Met Asn Glu Glu Val Glu Ile Phe
                275                 280                 285
Val Gly Pro His Pro Glu Gln Tyr Thr Trp Ile Leu Lys Leu Leu Lys
                290                 295                 300
Thr Arg Lys Pro Gly Glu Ile Gln Pro Tyr Lys Arg Lys Asp Leu Tyr
305                 310                 315                 320
Pro Ile Lys (2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

GTTGACTGGG AAGGTCTGGA G                                              21

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

CTGACCGCGC TCTATCGCGG                                                20
```

GENETICALLY MODIFIED TUMOR-TARGETED BACTERIA WITH REDUCED VIRULENCE

This application is a divisional of U.S. Ser. No. 10/125,328, filed Apr. 18, 2002, now U.S. Pat. No. 6,923,972, which is a continuation of U.S. Ser. No. 09/337,689, filed Jun. 22, 1999, now U.S. Pat. No. 6,475,482, issued Nov. 5, 2002, which is a divisional of U.S. Ser. No. 08/926,636, filed Sep. 10, 1997, now U.S. Pat. No. 6,080,849, issued on Jun. 27, 2000, the contents of which are incorporated herein by reference in their entirety.

1. FIELD OF THE INVENTION

The present invention is concerned with the isolation of a gene of *Salmonella* which, when genetically disrupted, reduces both virulence and septic shock caused by this organism and increases sensitivity to agents which promote eradication of the bacteria, e.g., chelating agents. The nucleotide sequence of this gene and the means for its genetic disruption are provided, and examples of the use of tumor-targeted bacteria which possess a disruption in this gene to inhibit growth of cancers, including, but not limited to, melanoma, colon cancer, and other solid tumors are described.

2. BACKGROUND OF THE INVENTION

Citation or identification of any reference in Section 2 of this application shall not be construed as an admission that such reference is available as prior art to the present invention.

A major problem in the chemotherapy of solid tumor cancers is delivery of therapeutic agents, such as drugs, in sufficient concentrations to eradicate tumor cells while at the same time minimizing damage to normal cells. Thus, studies in many laboratories are directed toward the design of biological delivery systems, such as antibodies, cytokines, and viruses for targeted delivery of drugs, pro-drug converting enzymes, and/or genes into tumor cells. Houghton and Colt, 1993, New Perspectives in Cancer Diagnosis and Management 1: 65-70; de Palazzo, et al., 1992a, Cell. Immunol. 142:338-347; de Palazzo et al., 1992b, Cancer Res. 52: 5713-5719; Weiner, et al., 1993a, J. Immunotherapy 13:110-116; Weiner et al., 1993b, J. Immunol. 151:2877-2886; Adams et al., 1993, Cancer Res. 53:4026-4034; Fanger et al., 1990, FASEB J. 4:2846-2849; Fanger et al., 1991, Immunol. Today 12:51-54; Segal, et al., 1991, Ann N.Y. Acad. Sci. 636:288-294; Segal et al., 1992, Immunobiology 185:390-402; Wunderlich et al., 1992; Intl. J. Clin. Lab. Res. 22:17-20; George et al., 1994, J. Immunol. 152:1802-1811; Huston et al., 1993, Intl. Rev. Immunol. 10:195-217; Stafford et al., 1993, Cancer Res. 53:4026-4034; Haber et al., 1992, Ann. N.Y. Acad. Sci. 667:365-381; Haber, 1992, Ann. N.Y. Acad. Sci. 667: 365-381; Feloner and Rhodes, 1991, Nature 349:351-352; Sarver and Rossi, 1993, AIDS Research & Human Retroviruses 9:483-487; Levine and Friedmann, 1993, Am. J. Dis. Child 147:1167-1176; Friedmann, 1993, Mol. Genetic Med. 3:1-32; Gilboa and Smith, 1994, Trends in Genetics 10:139-144; Saito et al., 1994, Cancer Res. 54:3516-3520; Li et al., 1994, Blood 83:3403-3408; Vieweg et al., 1994, Cancer Res. 54:1760-1765; Lin et al., 1994, Science 265:666-669; Lu et al., 1994, Human Gene Therapy 5:203-208; Gansbacher et al., 1992, Blood 80:2817-2825; Gastl et al., 1992, Cancer Res. 52:6229-6236.

2.1. Bacterial Infections and Cancer

Regarding bacteria and cancer, an historical review reveals a number of clinical observations in which cancers were reported to regress in patients with bacterial infections. Nauts et al., 1953, Acta Medica. Scandinavica 145:1-102, (Suppl. 276) state:

> The treatment of cancer by injections of bacterial products is based on the fact that for over two hundred years neoplasms have been observed to regress following acute infections, principally streptococcal. If these cases were not too far advanced and the infections were of sufficient severity or duration, the tumors completely disappeared and the patients remained free from recurrence.

Shear, 1950, J.A.M.A. 142:383-390 (Shear), observed that 75 percent of the spontaneous remissions in untreated leukemia in the Children's Hospital in Boston occurred following an acute episode of bacterial infection. Shear questioned:

> Are pathogenic and non-pathogenic organisms one of Nature's controls of microscopic foci of malignant disease, and in making progress in the control of infectious diseases, are we removing one of Nature's controls of cancer?

Subsequent evidence from a number of research laboratories indicated that at least some of the anti-cancer effects are mediated through stimulation of the host immune system, resulting in enhanced immuno-rejection of the cancer cells. For example, release of the lipopolysaccharide (LPS) endotoxin by gram-negative bacteria such as *Salmonella* triggers release of tumor necrosis factor, TNF, by cells of the host immune system, such as macrophages, Christ et al., 1995, Science 268:80-83. Elevated TNF levels in turn initiate a cascade of cytokine-mediated reactions which culminate in the death of tumor cells. In this regard, Carswell et al., 1975, Proc. Natl. Acad. Sci. USA 72:3666-3669, demonstrated that mice injected with *bacillus* Calmette-Guerin (BCG) have increased serum levels of TNF and that TNF-positive serum caused necrosis of the sarcoma Meth A and other transplanted tumors in mice. Further, Klimpel et al., 1990, J. Immunol. 145:711-717, showed that fibroblasts infected in vitro with *Shigella* or *Salmonella* had increased susceptibility to TNF.

As a result of such observations as described above, immunization of cancer patients with BCG injections is currently utilized in some cancer therapy protocols. See Sosnowski, 1994, Compr. Ther. 20:695-701; Barth and Morton, 1995, Cancer 75 (Suppl. 2):726-734; Friberg, 1993, Med. Oncol. Tumor. Pharmacother. 10:31-36 for reviews of BCG therapy.

2.2. Parasites and Cancer Cells

Although the natural biospecificity and evolutionary adaptability of parasites has been recognized for some time and the use of their specialized systems as models for new therapeutic procedures has been suggested, there are few reports of, or proposals for, the actual use of parasites as vectors.

Lee et al., 1992, Proc. Natl. Acad. Sci. USA 89:1847-1851 (Lee et al.) and Jones et al., 1992, Infect. Immun. 60:2475-2480 (Jones et al.) isolated mutants of *Salmonella typhimurium* that were able to invade HEp-2 (human epidermoid carcinoma) cells in vitro in significantly greater numbers than the wild type strain. The "hyperinvasive" mutants were isolated under conditions of aerobic growth of the bacteria that normally repress the ability of wild type strains to invade HEp-2 animal cells. However, Lee et al. and Jones et al. did not suggest the use of such mutants as therapeutic vectors, nor did they suggest the isolation of tumor-specific bacteria by selecting for mutants that show infection preference for melanoma or other cancers over normal cells of the body. Without tumor-specificity or other forms of attenuation, such hyperinvasive *Salmonella typhimurium* as described by Lee et al.

and Jones et al. would likely be pan-invasive, causing widespread infection in the cancer patient.

2.3. Tumor-Targeted Bacteria

Genetically engineered *Salmonella* have been demonstrated to be capable of tumor targeting, possess anti-tumor activity and are useful in delivering effector genes such as the herpes simplex thymidine kinase (HSV TK) to solid tumors (Pawelek et al., WO 96/40238). Two significant considerations for the in vivo use of bacteria are their virulence and ability to induce tumor necrosis factor α (TNFα)-mediated septic shock. As TNFα-mediated septic shock is among the primary concerns associated with bacteria, modifications which reduce this form of an immune response would be useful because TNFα levels would not become toxic, and a more effective concentration and/or duration of the therapeutic vector could be used.

2.4. Modified Bacterial Lipid A

Modifications to the lipid composition of tumor-targeted bacteria which alter the immune response as a result of decreased induction of TNFα production were suggested by Pawelek et al. (Pawelek et al., WO 96/40238). Pawelek et al. provided methods for isolation of genes from *Rhodobacter* responsible for monophosphoryl lipid A (MLA) production. MLA acts as an antagonist to septic shock. Pawelek et al. also suggested the use of genetic modifications in the lipid A biosynthetic pathway, including the mutation firA, which codes for the third enzyme UDP-3-O (R-30 hydroxylmyristoly)-glucosamine N-acyltransferase in lipid A biosynthesis (Kelley et al., 1993, J. Biol. Chem. 268: 19866-19874). Pawelek et al. showed that mutations in the firA gene induce lower levels of TNFα. However, these authors did not suggest enzymes which modify the myristate portion of the lipid A molecule. Furthermore, Pawelek et al. did not suggest that modifications to the lipid content of bacteria would alter their sensitivity to certain agents, such as chelating agents.

In *Escherichia coli*, the gene msbB (mlt) which is responsible for the terminal myristalization of lipid A has been identified (Engel, et al., 1992 J. Bacteriol. 174:6394-6403; Karow and Georgopoulos 1992 J. Bacteriol. 174: 702-710; Somerville et al., 1996 J. Clin. Invest. 97: 359-365). Genetic disruption of this gene results in a stable non-conditional mutation which lowers TNFα induction (Somerville et al., 1996 J. Clin. Invest. 97: 359-365). These references, however, do not suggest that disruption of the msbB gene in tumor-targeted *Salmonella* vectors would result in bacteria which are less virulent and more sensitive to chelating agents.

The problems associated with the use of bacteria as gene delivery vectors center on the general ability of bacteria to directly kill normal mammalian cells as well as their ability to overstimulate the immune system via TNFα which can have toxic consequences for the host (Bone, 1992 JAMA 268: 3452-3455; Dinarello et al., 1993 JAMA 269: 1829-1835). In addition to these factors, resistance to antibiotics can severely complicate coping with the presence of bacteria within the human body (Tschape, 1996 D T W Dtsch Tierarztl Wochenschr 1996 103:273-7; Ramos et al., 1996 Enferm Infec. Microbiol. Clin. 14: 345-51).

Hone and Powell, WO97/18837 ("Hone and Powell"), disclose methods to produce gram-negative bacteria having non-pyrogenic Lipid A or LPS. Although Hone and Powell broadly asserts that conditional mutations in a large number of genes including msbB, kdsA, kdsB, kdtA, and htrB, etc. can be introduced into a broad variety of gram-negative bacteria including *E. coli, Shigella* sp., *Salmonella* sp., etc., the only mutation exemplified is an htrB mutation introduced into *E. coli*. Further, although Hone and Powell propose the therapeutic use of non-pyrogenic *Salmonella* with a mutation in the msbB gene, there is no enabling description of how to accomplish such use. Moreover, Hone and Powell propose using non-pyrogenic bacteria only for vaccine purposes.

The objective of a vaccine vector is significantly different from the presently claimed tumor-targeted vectors. Thus, vaccine vectors have requirements quite different from tumor-targeted vectors. Vaccine vectors are intended to elicit an immune response. A preferred live bacterial vaccine must be immunogenic so that it elicits protective immunity; however, the vaccine must not be capable of excessive growth in vivo which might result in adverse reactions. According to the teachings of Hone and Powell, a suitable bacterial vaccine vector is temperature sensitive having minimal replicative ability at normal physiological ranges of body temperature.

In contrast, preferred tumor-targeted parasitic vectors, such as but not limited to *Salmonella*, are safely tolerated by the normal tissues of the body such that pathogenesis is limited, yet the vectors target to tumors and freely replicate within them. Thus, vaccine vectors which replicate minimally at normal body temperatures, would not be suitable for use as tumor-targeted vectors.

3. SUMMARY OF THE INVENTION

The present invention provides a means to enhance the safety of tumor-targeted bacteria, for example, by genetic modification of the lipid A molecule. The modified tumor-targeted bacteria of the present invention induce TNFα less than the wild type bacteria and have reduced ability to directly kill normal mammalian cells or cause systemic disease compared to the wild type strain. The modified tumor-targeted bacteria of the present invention have increased therapeutic efficacy, i.e., more effective dosages of bacteria can be used and for extended time periods due to the lower toxicity in the form of less induced TNFα and systemic disease.

The present invention provides compositions and methods for the genetic disruption of the msbB gene in bacteria, such as *Salmonella*, which results in bacteria, such as *Salmonella*, possessing a lesser ability to elicit TNFα and reduced virulence compared to the wild type. Additionally, the genetically modified bacteria have increased sensitivity to a chelating agent compared to bacteria with the wild type msbB gene. In a preferred embodiment, *Salmonella*, which are hyperinvasive to tumor tissues, are able to replicate within the tumors, and are useful for inhibiting the growth and/or reducing the tumor volume of sarcomas, carcinomas, lymphomas or other solid tumor cancers, such as germ line tumors and tumors of the central nervous system, including, but not limited to, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, and melanoma.

In an embodiment of the present invention, the bacteria are attenuated by other means, including but not limited to auxotrophic mutations. In another embodiment, the bacteria express pro-drug converting enzymes including but not limited to HSV-TK, cytosine deaminase (CD), and p450 oxidoreductase.

The present invention also provides a means for enhanced sensitivity for use in terminating therapy and for post therapy elimination. According to one embodiment of the present invention, the tumor-targeted bacteria having a genetically modified lipid A also have enhanced susceptibility to certain agents, e.g., chelating agents. It is a further advantage to modify tumor-targeted bacteria in this way because it increases the ability to eliminate the bacteria with agents which have an antibiotic-like effect, such as chelating agents including, but not limited to, Ethylenediaminetetraacetic Acid (EDTA), Ethylene Glycol-bis(β-aminoethyl Ether) N,N,N',N',-Tetraacetic Acid (EGTA), and sodium citrate. Modification to enhance the ability to eliminate the bacteria via exogenous means, such as the administration of an agent to which the genetically modified bacteria are more sensitive than their wild type counterparts, is therefore useful.

4. DEFINITIONS

As used herein, Salmonella encompasses all Salmonella species, including: *Salmonella typhi, Salmonella choleraesuis*, and *Salmonella enteritidis*. Serotypes of *Salmonella* are also encompassed herein, for example, *typhimurium*, a subgroup of *Salmonella enteritidis*, commonly referred to as *Salmonella typhimurium*.

Attenuation: Attenuation is a modification so that a microorganism or vector is less pathogenic. The end result of attenuation is that the risk of toxicity as well as other side-effects is decreased, when the microorganism or vector is administered to the patient.

Virulence: Virulence is a relative term describing the general ability to cause disease, including the ability to kill normal cells or the ability to elicit septic shock (see specific definition below).

Septic shock: Septic shock is a state of internal organ failure due to a complex cytokine cascade, initiated by TNFα. The relative ability of a microorganism or vector to elicit TNFα is used as one measure to indicate its relative ability to induce septic shock.

Chelating agent sensitivity: Chelating agent sensitivity is defined as the effective concentration at which bacteria proliferation is affected, or the concentration at which the viability of bacteria, as determined by recoverable colony forming units (c.f.u.), is reduced.

5. BRIEF DESCRIPTION OF THE FIGURES

The present invention may be understood more fully by reference to the following detailed description, illustrative examples of specific embodiments and the appended figures.

FIGS. 1A-1B. The complete DNA sequence of the *Salmonella* wild-type (WT) 14028 msbB gene (SEQ ID NO:1) and the deduced amino acid sequence of the encoded protein (SEQ ID NO:2).

FIGS. 2A-2C. Knockout construct generated using the cloned *Salmonella* WT 14028 msbB gene. The cloned gene was cut with SphI and MluI thereby removing approximately half of the msbB coding sequence, and the tetracycline resistance gene (TET) from pBR322 cut with AatII and AvaI was inserted after blunt-ending using the Klenow fragment of DNA polymerase I. A=Knockout construct. B=*Salmonella* chromosomal copy of msbB. C=*Salmonella* disrupted chromosomal copy of msbB after homologous recombination. The start codon (ATG) and stop codon (TAA) and restriction sites AseI, BamHI, SphI, MluI, and EcoRV are shown. The position of two primers, P1 and P2 which generate two different sized PCR products for either wild type or disrupted msbB are shown.

FIGS. 3A-3C. Southern blot analysis of chromosomally disrupted *Salmonella* WT 14028 msbB. A) Southern blot probed with the tetracycline gene, demonstrating its presence in the plasmid construct and the two clones, and its absence in the WT 14028 bacteria. B) Southern blot of a similar gel probed with an $^{32}$P-labeled AseI/BamH1 fragment derived from the cloned msbB. The AseI enzyme cuts upstream of msbB, and the BamH1 cuts in one location in the wild type, but in a second location in the tetracycline gene which results in a higher molecular weight product. Lane 1 (KO) shows the position of the band in the knockout construct, compared to the WT 14028 in lane 2 (WT). Lanes 3 and 4 show the clones YS8211 and YS861 with a higher molecular weight product. C) Southern blot of a similar gel probed with an $^{32}$P-labeled mluI fragment derived from the cloned msbB. See text Section 7.2 for details.

FIG. 4. TNFα induction by live *Salmonella* WT 14028 in mice. $1\times10^8$ live bacteria in 0.1 cc phosphate buffered saline of the wild type or msbB$^-$ disrupted strains were injected i.v. in the tail vein of Balb/c mice. The bar graph indicates the TNFα induction with error bars. Clone YS8211 induces TNFα 32% compared to *Salmonella* WT 14028.

Figure 5:
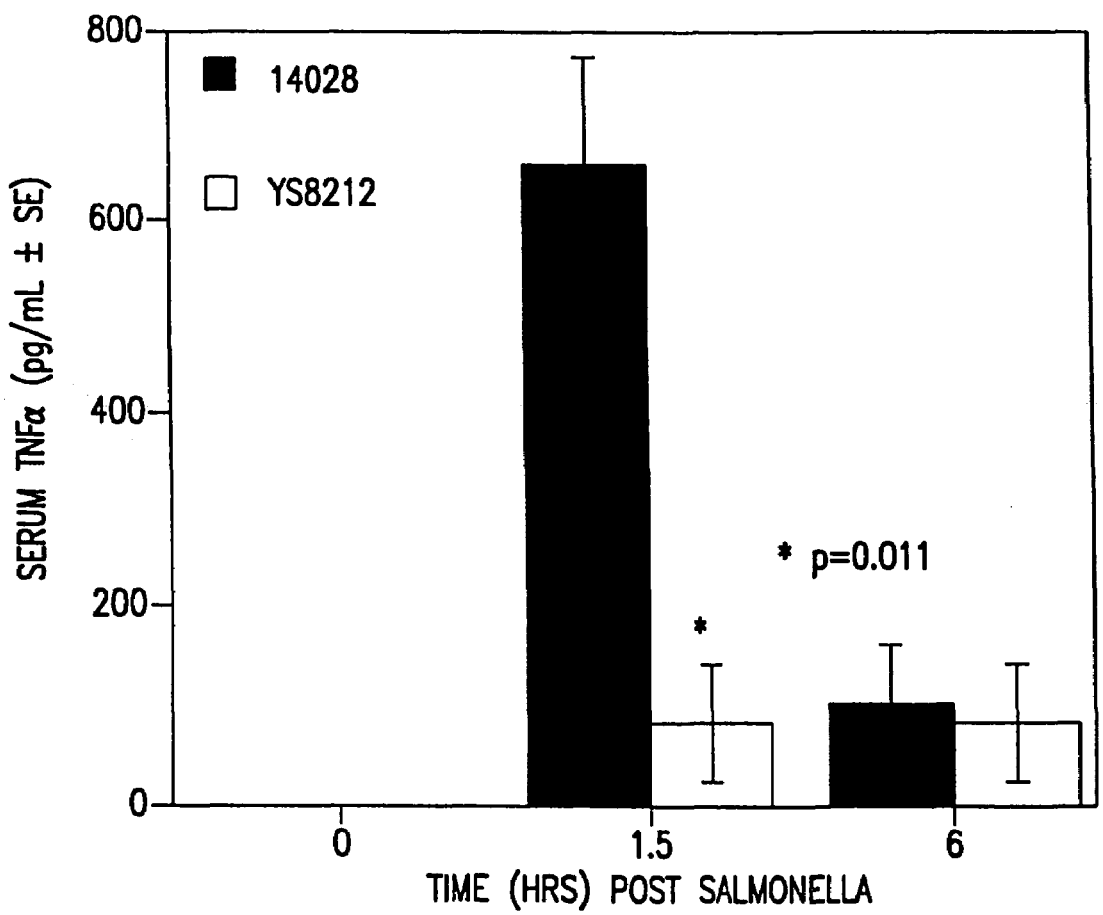

FIG. 5. TNFα response by Sinclair swine to live *Salmonella* WT 14028 and msbB$^-$ clone YS8212. TNFα levels were measured at 1.5 and 6.0 hours following i.v. introduction of $1\times10^9$ c.f.u. *Salmonella* WT 14028 and YS8212. At 1.5 hours TNFα response was significantly lower ($p\leq0.011$) in the msbB deletion mutant compared to the wild type.

Figure 6A:
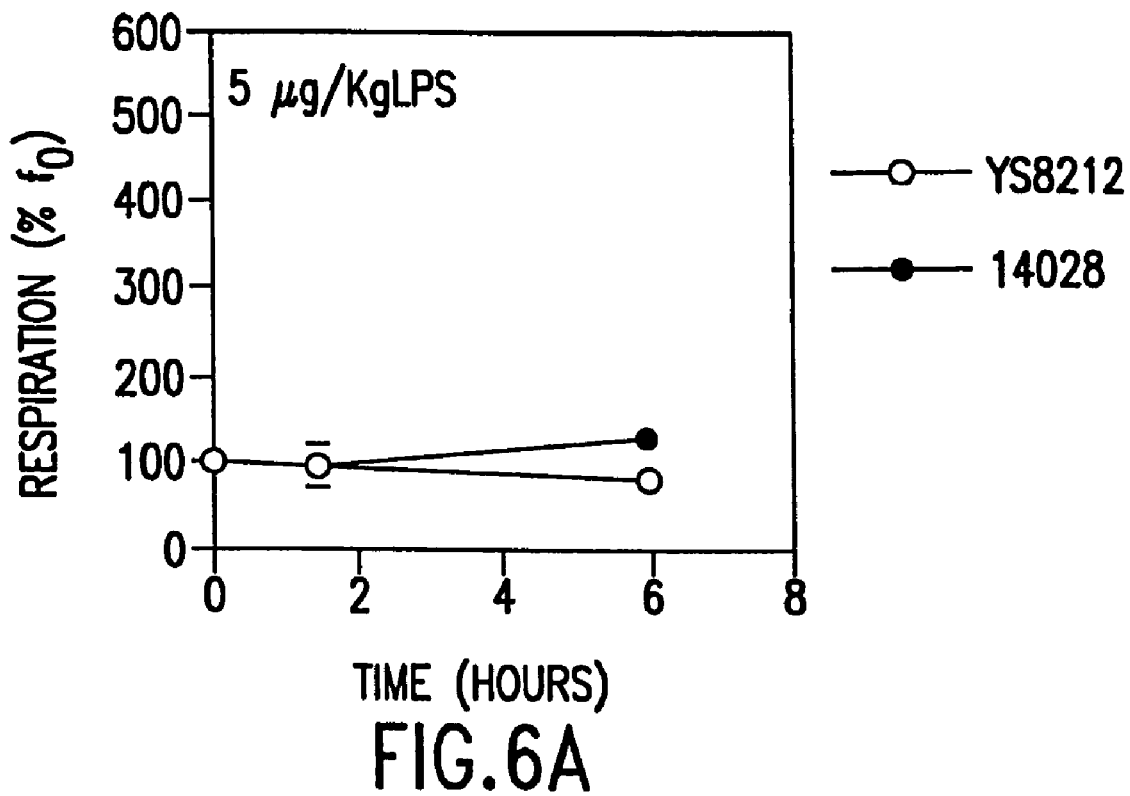
Figure 6B:
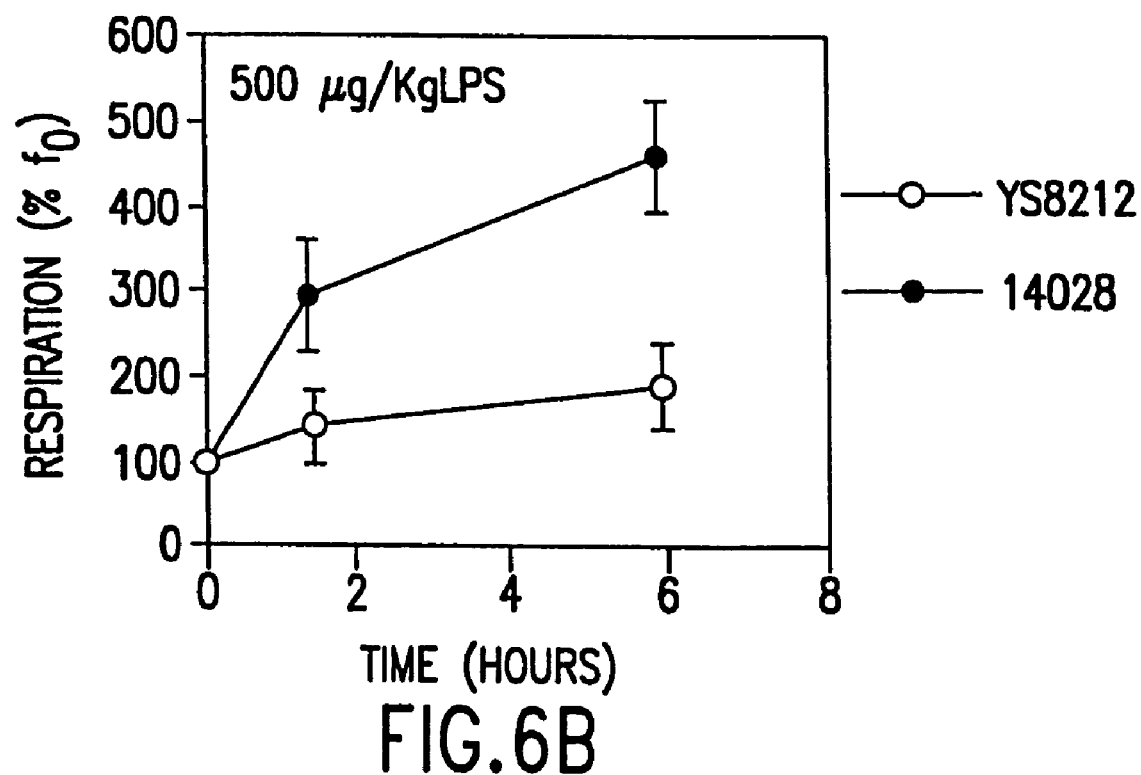

FIGS. 6A-6B. Respiratory level changes induced by LPS from WT 14028 and msbB clone YS8212. Sinclair swine were injected with 5 or 500 μg/kg purified LPS and respiration rate was determined. The 500 μg/kg of LPS from *Salmonella* WT 14028 raised the rate of respiration to more than 4 times normal, whereas the rate of respiration in msbB$^-$ LPS-treated animals was less than doubled.

Figure 7:
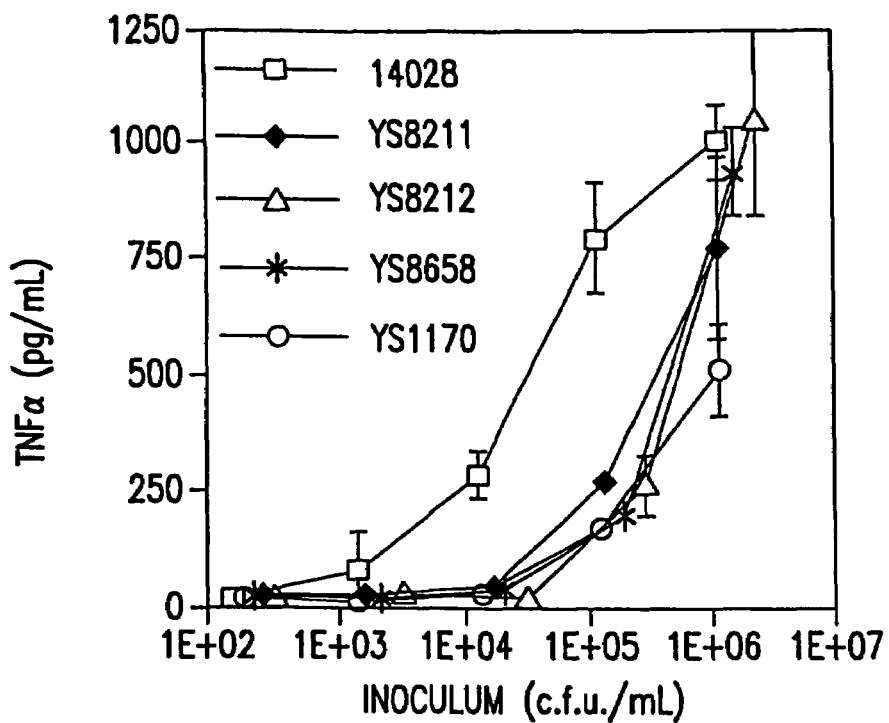

FIG. 7. TNFα induction by live *Salmonella* WT 14028 in human monocytes. Human monocytes isolated from peripheral blood were exposed to increasing amounts of *Salmonella* c.f.u. At $1.0\times10^5$ c.f.u., concentrations of TNFα induced by WT 14028 were more than 3 times higher than those induced by a number of msbB$^-$ clones, i.e., YS8211, YS8212, YS8658, and YS1170.

Figure 8:
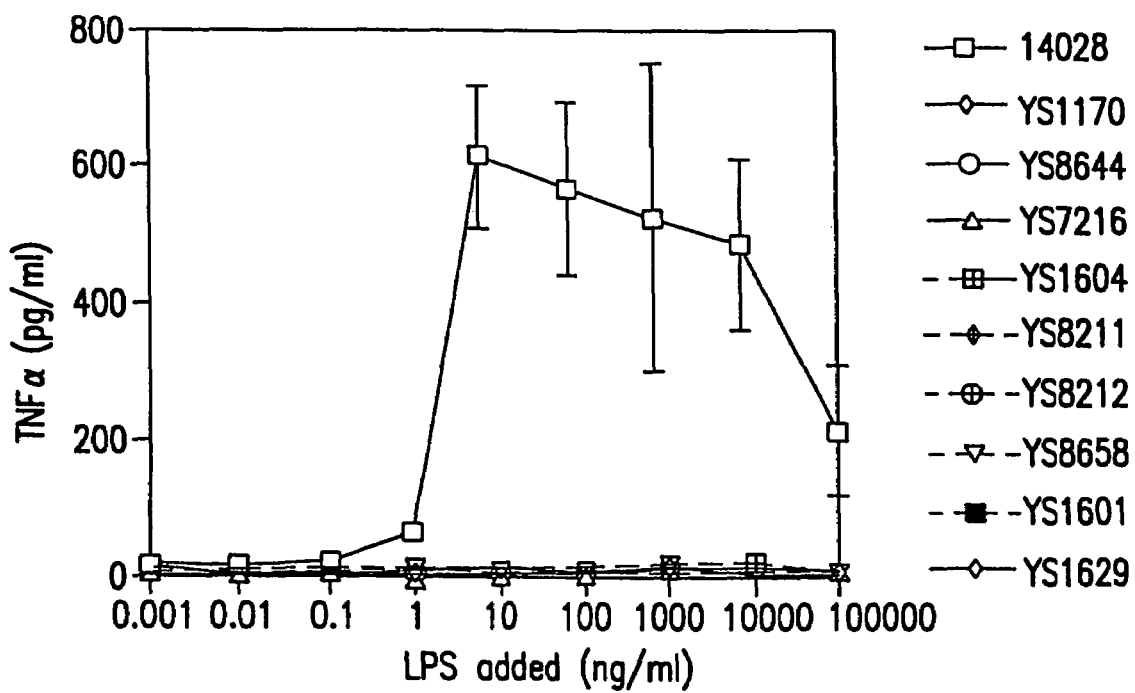

FIG. 8. TNFα production by human monocytes. Human monocytes isolated from peripheral blood were exposed to increasing amounts of purified LPS. As little as 1 nanogram of LPS from wild type was sufficient to elicit a measurable TNFα response and was maximal at 10 ng. In contrast, 100 μg of LPS from each of a number of msbB$^-$ clones was insufficient to generate any response. Thus, at 10 ng LPS, the concentration of TNFα induced by *Salmonella* WT 14028 was at least $10^5$ times higher than concentrations of TNFα induced by the independent msbB knockouts, i.e., YS7216 and YS8211, and the derivatives, i.e., YS1170, YS8644, YS1604, YS8212, YS8658, YS1601, YS1629.

Figure 9A:
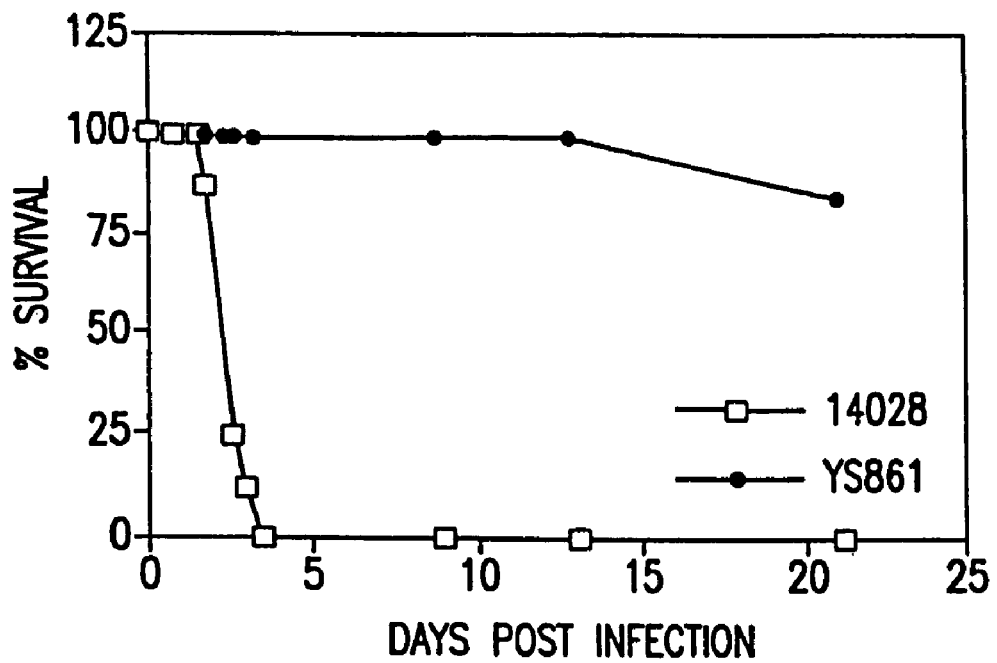
Figure 9B:
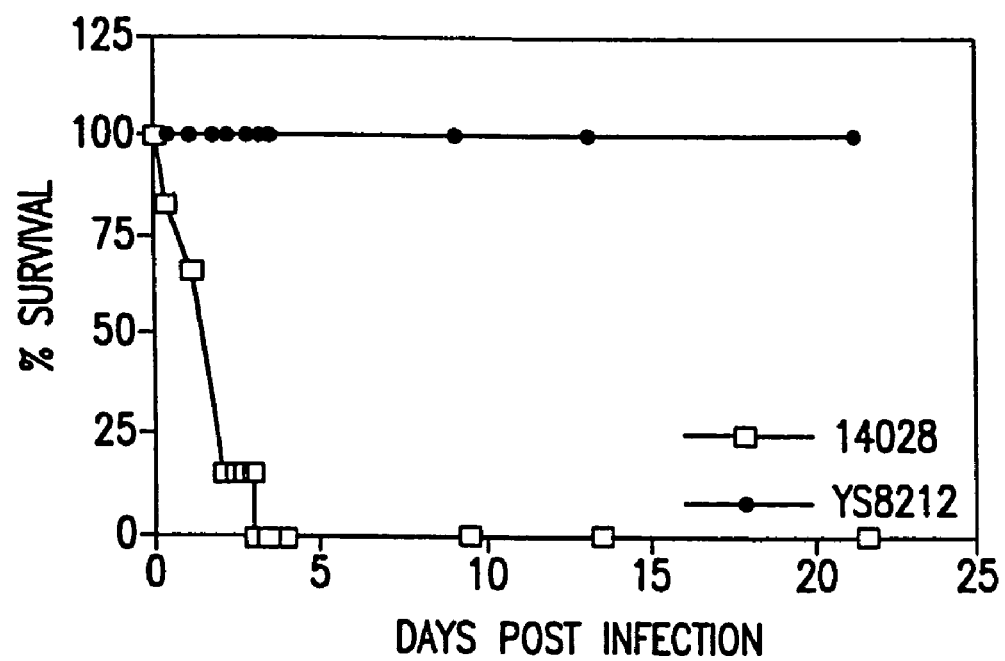

FIGS. 9A-9B. Survival of mice and Sinclair swine, injected with $2\times10^7$ or $1\times10^9$ respectively of live bacteria. A) WT 14028 killed all the mice in 4 days, whereas the msbB$^-$ clone YS862 spared 90% of the mice past 20 days. B) Similarly, WT 14028 killed all the swine in 3 days, whereas the msbB– clone YS8212 spared 100% of the swine past 20 days.

Figure 10:
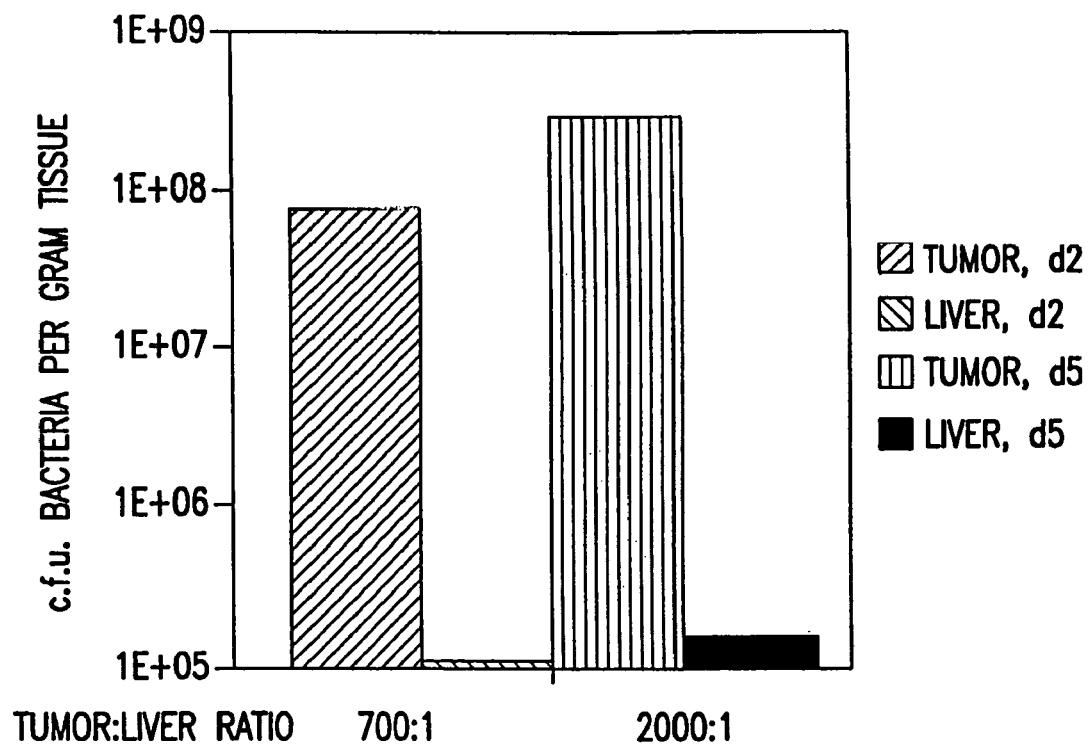

FIG. 10. Biodistribution of msbB$^-$ *Salmonella* YS8211 in B16F10 melanoma tumors. At 5 days, the ratio of msbB$^-$ *Salmonella* within the tumors compared to those in the liver exceeded 1000:1.

Figure 11:
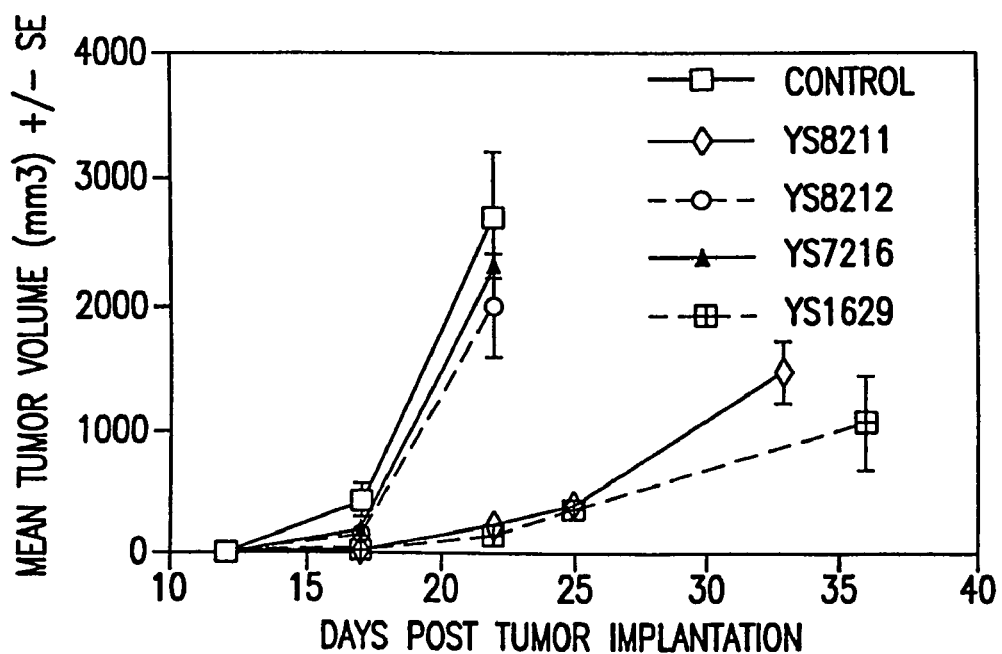

FIG. 11. Tumor retardation by msbB$^-$ *Salmonella*. B16F10 melanoma tumors were implanted in the flank of C57BL/6 mice and allowed to progress to day 8. Mice either received no bacteria (control) or msbB$^-$ strains YS8211, YS8212, YS7216, YS1629. Two of the strains, YS8211 and YS1629 retarded tumor progression significantly, whereas strains YS7216 and YS8212 did not.

Figure 12A:
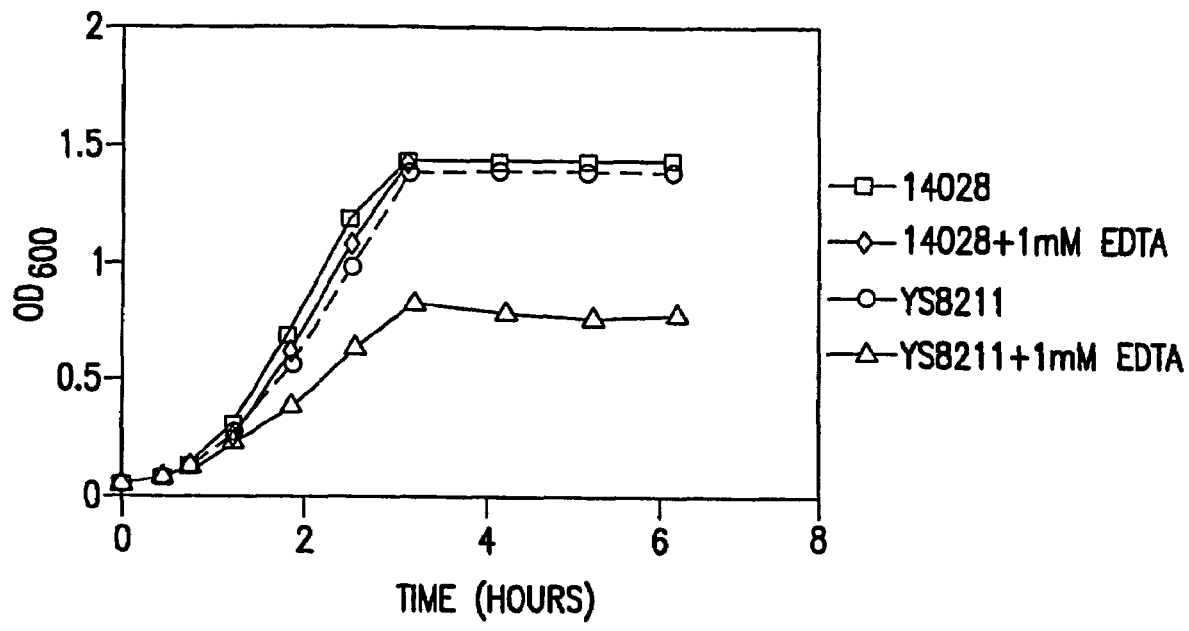
Figure 12B:
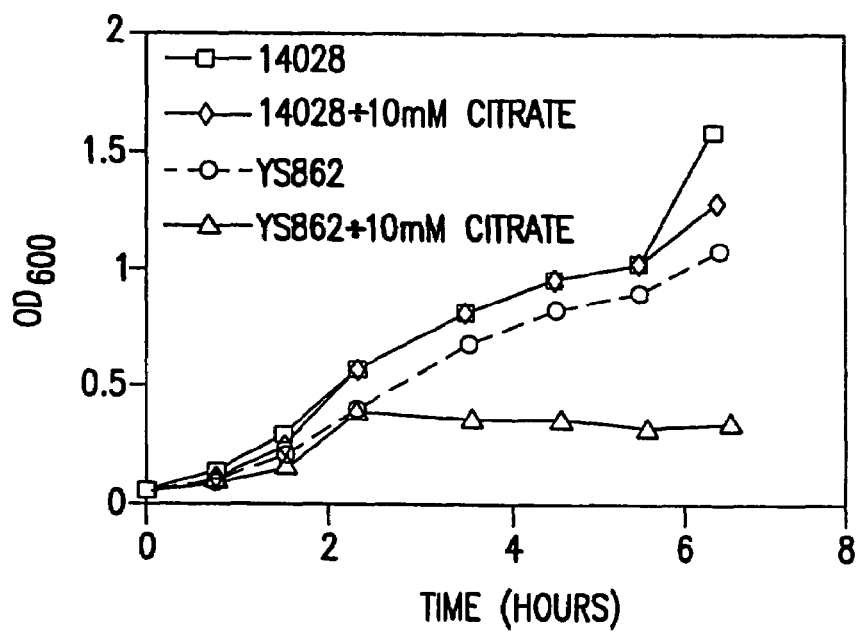

FIGS. 12A-12B. Sensitivity of WT 14028 and msbB disrupted bacteria to chelating agents. Wild type and msbB disrupted *Salmonella* clone YS8211 and YS862 were grown in LB broth lacking sodium chloride (LB-zero), in the presence or absence of 1 mM EDTA (FIG. 12A) or in the presence or absence of 10 mM sodium citrate (FIG. 12B). The $OD_{600}$ was determined and plotted as a function of time. The msbB+ strain showed little inhibition by EDTA or sodium citrate, compared to the msbB⁻ strains which showed near complete cessation of growth after 3 hours for EDTA or sodium citrate.

Figure 13A:
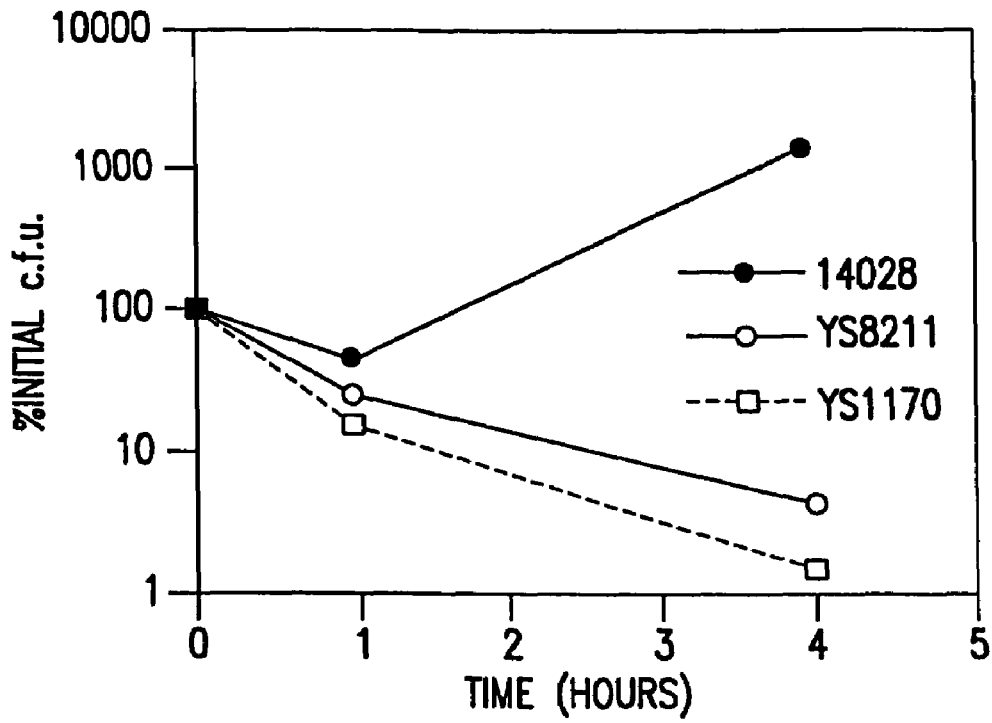
Figure 13B:
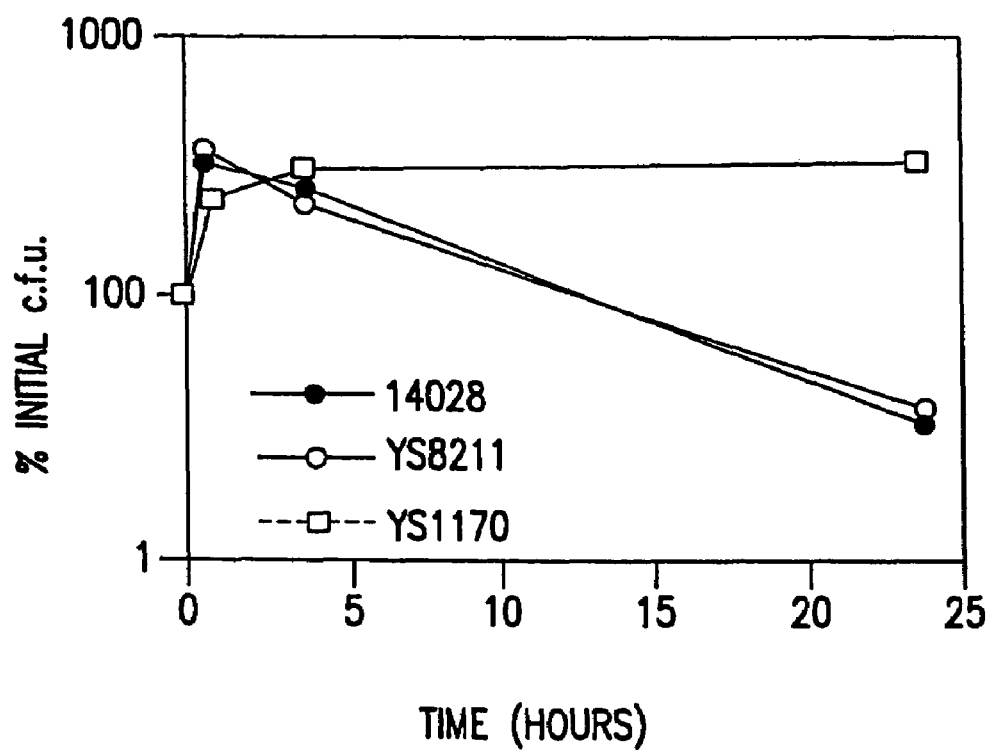

FIGS. 13A-13B. Survival of msbB⁻ bacteria within murine macrophages. Murine bone marrow-derived macrophages (FIG. 13A) and a murine macrophage cell line, J774, (FIG. 13B) were used as hosts for bacterial internalization and quantified over time. The data are presented as a percentage of initial c.f.u.

6. DETAILED DESCRIPTION OF THE INVENTION

The present invention is based on the isolation of a gene of Salmonella, i.e., msbB, which, when present in its normal form, contributes to TNFα induction, general virulence, survival within macrophages, and insensitivity to certain agents which promote eradication of the bacteria. The present invention is directed to the genetic modification of the gene which results in disrupting the normal function of the product of the gene, and the incorporation of the genetic modification into tumor-targeted bacteria, including Salmonella, for therapeutic use. In a preferred embodiment, the genetically modified bacteria are used in animals, including humans, for reduction of volume and/or growth inhibition of solid tumors.

In a preferred embodiment, bacteria useful for the present invention show preference for attachment to and penetration into certain solid tumor cancer cells or have an enhanced propensity to proliferate in tumor tissues as compared to normal tissues. These bacteria, including but not limited to Salmonella, having a natural ability to distinguish between cancerous or neoplastic cells tissues and normal cells/tissues.

Alternatively, tumor cell-specific bacteria useful for the invention may be selected for and/or improved in tumor targeting ability using the methods described by Pawelek et al., WO 96/40238 incorporated herein by reference. Pawelek et al. describe methods for isolating tumor cell-specific bacteria by cycling a microorganism through a pre-selected target cell, preferably a solid tumor cell in vitro, or through a solid tumor in vivo, using one or more cycles of infection.

6.1. Isolation/Identification of a Gene Involved in Virulence

The E. coli gene, msbB, has been shown to be involved in myristilization of lipid A (Somerville et al., 1996, J. Clin. Invest. 97:359-365.) The chromosomal organization of the E. coli msbB gene and the DNA sequence coding for the msbB gene have been described (Engel, et al., 1992, J. Bacteriol. 174:6394-6403; Karow and Georgopoulos, 1992, J. Bacteriol. 174: 702-710; Somerville et al., 1996, J. Clin. Invest. 97: 359-365). However, this gene or a homologue has not been isolated from other species of bacteria.

As shown in the present invention, the msbB gene can be isolated from bacterial strains, other than E. coli, using low stringency DNA/DNA hybridization techniques known to those skilled in the art. (Sambrook et al., Molecular Cloning, Cold Spring Harbor Laboratory Press, 1989). For an illustrative example of isolation of a msbB gene of bacteria, including but not limited to Salmonella spp., see Section 7.1 infra. A bacterial DNA library can be probed with a $^{32}$P-labeled msbB gene from E. coli. Hybridizing clones are determined to be correct if they contain DNA sequences similar to the known E. coli msbB gene.

6.1.1. Genetic Alteration of Salmonella msbB

One embodiment of the present invention provides a composition of matter which is a strain of bacteria with a genetic alteration in the msbB gene. In a preferred embodiment, the bacteria is Salmonella sp. Genetic alteration in the form of disruption or deletion can be accomplished by several means known to those skilled in the art, including homologous recombination using an antibiotic sensitivity marker. These methods involve disruption of the plasmid-based, cloned msbB gene using restriction endonucleases such that part or all of the gene is disrupted or eliminated or such that the normal transcription and translation are interrupted, and an antibiotic resistance marker for phenotypic selection is inserted in the region of that deletion, disruption or other alteration. Linearized DNA is transformed into Salmonella, and bacteria bearing the antibiotic resistance are further examined for evidence of genetic alteration. Means for examining genetic alteration include PCR analysis and Southern blotting. For an illustrative example of genetic disruption of a Salmonella msbB gene, see Section 7.2.

In another embodiment of the invention, the msbB–/antibiotic sensitivity marker can be transduced into a new bacterial strain. An illustrative example is provided in Section 7.2. Bacteriophage P22 and a Salmonella msbB⁻ clone can be grown in zero salt Luria broth and the new phages in the supernate can be used to infect a new Salmonella strain.

Yet another embodiment of the present invention provides Salmonella that are attenuated in more than one manner, e.g., a mutation in the pathway for lipid A production, such as the msbB mutation described herein and one or more mutations to auxotrophy for one or more nutrients or metabolites, such as uracil biosynthesis, purine biosynthesis, and arginine biosynthesis as described by Bochner, 1980, J. Bacteriol. 143: 926-933 herein incorporated by reference. In a preferred embodiment, the ability of msbB⁻ Salmonella to accumulate within tumors is retained by msbB– Salmonella having one or more auxotrophic mutations. In a more preferred mode of this embodiment of the invention, the bacterial vector which selectively targets tumors and expresses a pro-drug converting enzyme is auxotrophic for uracil, aromatic amino acids, isoleucine and valine and synthesizes an altered lipid A.

6.1.2. Characteristics of Salmonella Having Disrupted msbB

Reduction of TNFα Induction

A characteristic of the msbB⁻ Salmonella, described herein, is decreased ability to induce a TNFα response compared to the wild type bacterial vector. Both the whole bacteria and isolated or purified lipopolysaccharide (LPS) elicit a TNFα response. In an embodiment of the invention, the msbB⁻ Salmonella induces TNFα expression at about 5 percent to about 40 percent compared to the wild type Salmonella sp. (in other words, the msbB⁻ Salmonella induces TNFα expression at about 5 percent to about 40 percent of the level induced by wild type Salmonella, e.g., WT 14028.) In a preferred embodiment of the invention, the msbB⁻ Salmonella induces TNFα expression at about 10 percent to about 35 percent of that induced by a wild type Salmonella sp. In an embodiment of the invention, purified LPS from msbB⁻ Salmonella induces TNFα expression at a level which is less than or equal to 0.001 percent of the level induced by LPS purified from wild type Salmonella sp. TNFα response induced by whole bacteria or isolated or purified LPS can be assessed in vitro or in vivo using commercially available assay systems such as by enzyme linked immunoassay (ELISA). For illustrative examples, see sections 7.3.1 and 7.3.2 infra. Comparison of TNFα production on a per c.f.u. or on a µg/kg basis, is used to determine relative activity. Lower TNFα levels on a per unit basis indicate decreased induction of TNFα production.

Reduction of Virulence

Another characteristic of the msbB$^-$ *Salmonella*, described herein, is decreased virulence towards the host cancer patient compared to the wild type bacterial vector. Wild type *Salmonella* can under some circumstances exhibit the ability to cause significant progressive disease. Acute lethality can be determined for normal wild type live *Salmonella* and live msbB$^-$ *Salmonella* using animal models. For an illustrative example, see Section 7.4 and Section 9, Table III. Comparison of animal survival for a fixed inoculum is used to determine relative virulence. Strains having a higher rate of survival have decreased virulence.

Decreased Survival within Macrophages

Another characteristic of msbB$^-$ *Salmonella* described herein, is decreased survival within macrophage cells as compared to survival of wild type bacteria. Wild type *Salmonella* (e.g., ATCC 14028) are noted for their ability to survive within macrophages (Baumler, et al., 1994, Infect. Immun. 62:1623-1630; Buchmeier and Heffron 1989, Infect. Immun. 57:1-7; Buchmeier and Heffron, 1990, Science 248:730-732; Buchmeier et al., 1993, Mol. Microbiol. 7:933-936; Fields et al., 1986, Proc. Natl. Acad. Sci. USA 83:5189-93; Fields et al., 1989, Science 243:1059-62; Fierer et al., 1993, Infect. Immun. 61:5231-5236; Lindgren et al., 1996, Proc. Natal. Acad. Sci. USA 3197-4201; Miller et al., 1989, Proc. Natl. Acad. Sci. USA 86:5054-5058; Sizemore et al., 1997, Infect. Immun. 65:309-312).

A comparison of survival time in macrophages can be made using an in vitro cell culture assay. A lower number of c.f.u. over time is indicative of reduced survival within macrophages. For an illustrative example, see Section 8 infra. As shown therein, using the gentamicin-based internalization assay and bone marrow-derived murine macrophages or the murine macrophage cell line J774, a comparison of survival of WT 14028 and msbB$^-$ clone YS8211 was determined. In an embodiment of the invention, survival occurs at about 50 percent to about 30 percent; preferably at about 30 percent to about 10 percent; more preferably at about 10 percent to about 1 percent of survival of the wild type stain.

Increased Sensitivity

Another characteristic of one embodiment of the msbB$^-$ *Salmonella*, described herein, is increased sensitivity of the tumor-targeted bacteria to specific chemical agents which is advantageously useful to assist in the elimination of the bacteria after administration in vivo. Bacteria are susceptible to a wide range of antibiotic classes. However, it has surprisingly been discovered that certain *Salmonella* msbB$^-$ mutants encompassed by the present invention are sensitive to certain chemicals which are not normally considered antibacterial agents. In particular, certain msbB$^-$ *Salmonella* mutants are more sensitive than WT 14028 to chelating agents.

Previous descriptions of msbB$^-$ *E. coli* have not suggested increased sensitivity to such chelating agents. To the contrary, reports have included increased resistance to detergents such as deoxycholate (Karow and Georgopoulos 1992 J. Bacteriol. 174: 702-710).

To determine sensitivity to chemical agents, normal wild type bacteria and msbB$^-$ bacteria are compared for growth in the presence or absence of a chelating agent, for example, EDTA, EGTA or sodium citrate. Comparison of growth is measured as a function of optical density, i.e., a lower optical density in the msbB$^-$ strain grown in the presence of an agent, than when the strain is grown in its absence, indicates sensitivity. Furthermore, a lower optical density in the msbB$^-$ strain grown in the presence of an agent, compared to the msbB$^+$ strain grown in its presence, indicates sensitivity specifically due to the msbB mutation. For an illustrative example, see section 7.7 infra. In an embodiment of the invention, 90 percent inhibition of growth of msbB– *Salmonella* (compared to growth of wild type *Salmonella* sp.) occurs at about 0.25 mM EDTA to about 0.5 mM EDTA, preferably at about 99 percent inhibition at about 0.25 mM EDTA to above 0.5 mM EDTA, more preferably at greater than 99 percent inhibition at about 0.25 mM EDTA to about 0.5 mM EDTA. Similar range of growth inhibition is observed at similar concentrations of EDTA.

Derivatives of msbB Mutants

When grown in Luria Broth (LB) containing zero salt, the msbB$^-$ mutants of the present invention are stable, i.e., produce few derivatives (as defined below). Continued growth of the msbB$^-$ mutants on modified LB (10 g tryptone, 5 g yeast extract, 2 ml 1N CaCl$_2$, and 2 ml 1N MgSO$_4$ per liter, adjusted to pH 7 using 1N NaOH) also maintains stable mutants. In contrast, when grown in normal LB, the msbB$^-$ mutants may give rise to derivatives. As used herein, "derivatives" is intended to mean spontaneous variants of the msbB$^-$ mutants characterized by a different level of virulence, tumor inhibitory activity and/or sensitivity to a chelating agent when compared to the original msbB$^-$ mutant. The level of virulence, tumor inhibitory activity, and sensitivity to a chelating agent of a derivative may be greater, equivalent, or less compared to the original msbB$^-$ mutant.

Derivatives of msbB$^-$ strains grow faster on unmodified LB than the original msbB$^-$ strains. In addition, derivatives can be recognized by their ability to grow on MacConkey agar (an agar which contains bile salts) and by their resistance to chelating agents, such as EGTA and EDTA. Derivatives can be stably preserved by cryopreservation at −70° C. or lyophilization according to methods well known in the art (Cryz et al., 1990, In New Generation Vaccines, M. M. Levine (ed.), Marcel Dekker, New York pp. 921-932; Adams, 1996, In Methods in Molecular Medicine: Vaccine Protocols, Robinson et al. (eds), Humana Press, New Jersey, pp. 167-185; Griffiths, Id. pp. 269-288.)

Virulence is determined by evaluation of the administered dose at which half of the animals die (LD$_{50}$). Comparison of the LD$_{50}$ of the derivatives can be used to assess the comparative virulence. Decrease in the LD$_{50}$ of a spontaneous derivative as compared to its msbB$^-$ parent, indicates an increase in virulence. In an illustrative example, the faster-growing derivatives either exhibit the same level of virulence, a greater level of virulence, or a lower level of virulence compared to their respective original mutant strains (see Section 9, Table III.) In another example, the ability of a derivative to induce TNFα remains the same as the original mutant strain (see Section 7.3, FIG. 7).

In an illustrative example, the derivatives can either inhibit tumor growth more than or less than their respective original mutant strains (see Section 7.6, FIG. 11). It is demonstrated in Section 7.6 that the original msbB$^-$ mutant, YS8211, significantly inhibits tumor growth whereas a derivative of this clone, YS8212, has less tumor growth inhibition activity. In contrast, the derivative, YS1629, exhibits enhanced tumor growth inhibition activity compared to its parent msbB⁻ clone, YS7216.

A derivative which is more virulent than its parent mutant but which does induce TNFα at a lower level when compared to the wild type, i.e., at a level of about 5 percent to about 40 percent of that induced by the wild type *Salmonella*, can be further modified to contain one or more mutations to auxotrophy. In an illustrative example, the YS1170 derivative is mutated such that it is auxotrophic for one or more aromatic amino acids, e.g., aroA, and thus can be made less virulent and is useful according to the methods of the present invention.

Prior to use of a derivative in the methods of the invention, the derivative is assessed to determine its level of virulence, ability to induce TNFα, ability to inhibit tumor growth, and sensitivity to a chelating agent.

6.2. Use of *Salmonella* with Disrupted msbB for Tumor Targeting and In Vivo Treatment of Solid Tumors According to the present invention, the msbB⁻ mutant *Salmonella* are advantageously used in methods to produce a tumor growth inhibitory response or a reduction of tumor volume in an animal including a human patient having a solid tumor cancer. For such applications, it is advantageous that the msbB⁻ mutant *Salmonella* possess tumor targeting ability or target preferably to tumor cells/tissues rather than normal cells/tissues. Additionally, it is advantageous that the msbB⁻ mutant *Salmonella* possess the ability to retard or reduce tumor growth and/or deliver a gene or gene product that retards or reduces tumor growth. Tumor targeting ability can be assessed by a variety of methods known to those skilled in the art, including but not limited to cancer animal models.

For example, *Salmonella* with a msbB⁻ modification are assayed to determine if they possess tumor targeting ability using the B16F10 melanoma subcutaneous animal model. A positive ratio of tumor to liver indicates that the genetically modified *Salmonella* possesses tumor targeting ability. For an illustrative example, see Section 7.5.

*Salmonella* with the msbB⁻ modification can be assayed to determine if they possess anti-tumor ability using any of a number of standard in vivo models, for example, the B16F10 melanoma subcutaneous animal model. By way of an illustrative example, and not by way of limitation, tumors are implanted in the flanks of mice and staged to day 8 and then bacterial strains are injected i.p. Tumor volume is monitored over time. Anti-tumor activity is determined to be present if tumors are smaller in the bacteria-containing groups than in the untreated tumor-containing animals. For an illustrative example, see section 7.6 infra.

The *Salmonella* of the present invention for in vivo treatment are genetically modified such that, when administered to a host, the bacteria is less toxic to the host and easier to eradicate from the host's system. The *Salmonella* are superinfective, attenuated and specific for a target tumor cell. In a more preferred embodiment, the *Salmonella* may be sensitive to chelating agents having antibiotic-like activity.

In addition, the *Salmonella* used in the methods of the invention can encode "suicide genes", such as pro-drug converting enzymes or other genes, which are expressed and secreted by the *Salmonella* in or near the target tumor. Table 2 of Pawelek et al. WO96/40238 at pages 34-35 presents an illustrative list of pro-drug converting enzymes which are usefully secreted or expressed by msbB⁻ mutant *Salmonella* for use in the methods of the invention. Table 2 and pages 32-35 are incorporated herein by reference. The gene can be under the control of either constitutive, inducible or cell-type specific promoters. See Pawelek et al. at pages 35-43, incorporated herein by reference, for additional promoters, etc. useful for mutant *Salmonella* for the methods of the present invention. In a preferred embodiment, a suicide gene is expressed and secreted only when a *Salmonella* has invaded the cytoplasm of the target tumor cell, thereby limiting the effects due to expression of the suicide gene to the target site of the tumor.

In a preferred embodiment, the *Salmonella*, administered to the host, expresses the HSV TK gene. Upon concurrent expression of the TK gene and administration of ganciclovir to the host, the ganciclovir is phosphorylated in the periplasm of the microorganism which is freely permeable to nucleotide triphosphates. The phosphorylated ganciclovir, a toxic false DNA precursor, readily passes out of the periplasm of the microorganism and into the cytoplasm and nucleus of the host cell where it incorporates into host cell DNA, thereby causing the death of the host cell.

The method of the invention for inhibiting growth or reducing volume of a solid tumor comprises administering to a patient having a solid tumor, an effective amount of an isolated mutant *Salmonella* sp. comprising a genetically modified msbB gene, said mutant being capable of targeting to the solid tumor when administered in vivo. The msbB⁻ mutant *Salmonella* may also express a suicide gene as described above.

In addition, in one embodiment the isolated *Salmonella* is analyzed for sensitivity to chelating agents to insure for ease in eradication of the *Salmonella* from the patient's body after successful treatment or if the patient experiences complications due to the administration of the isolated *Salmonella*. Thus, if *Salmonella* is employed which is sensitive to a chelating agent, at about 0.25 mM to about 1.0 mM of a chelating agent such as EGTA, EDTA or sodium citrate can be administered to assist in eradication of the *Salmonella* after the anti-tumor effects have been achieved.

When administered to a patient, e.g., an animal for veterinary use or to a human for clinical use, the mutant *Salmonella* can be used alone or may be combined with any physiological carrier such as water, an aqueous solution, normal saline, or other physiologically acceptable excipient. In general, the dosage ranges from about 1.0 c.f.u./kg to about $1\times10^{10}$ c.f.u./kg; optionally from about 1.0 c.f.u./kg to about $1\times10^{8}$ c.f.u./kg; optionally from about $1\times10^{2}$ c.f.u./kg to about $1\times10^{8}$ c.f.u./kg; optionally from about $1\times10^{4}$ c.f.u./kg to about $1\times10^{8}$ c.f.u./kg.

The mutant *Salmonella* of the present invention can be administered by a number of routes, including but not limited to: orally, topically, injection including, but limited to intravenously, intraperitoneally, subcutaneously, intramuscularly, intratumorally, i.e., direct injection into the tumor, etc.

The following series of examples are presented by way of illustration and not by way of limitation on the scope of the invention.

7. EXAMPLE

Loss of Virulence, Reduced TNFα Stimulation, and Increased Chelating Agent Sensitivity, by Disruption of the *Salmonella* msbB 7.1. Isolation and Composition of *Salmonella* msbB Gene A *Salmonella* genomic DNA library was first constructed. Wild type *Salmonella typhimurium* (ATCC strain 14028) were grown overnight and genomic DNA extracted according to the methods of Sambrook et al. (Molecular Cloning: A Laboratory Manual, 2nd Ed., Cold Spring Harbor Press, Cold Spring Harbor, 1989). Size-selected restriction endonuclease-digested fragments ranging from 2 to 10 kB were generated by time-limited digestion with Sau3A and selected by agarose gel electrophoresis. These fragments were ligated into pBluescript SK– and transformed to *E. coli* DH5α. Random analysis of clones revealed DNA inserts in ≧87%, with average size=5.1 Kb. The library consisted of $1.4 \times 10^4$ independent clones. In order to reduce the hybridization of the *E. coli*-originated msbB probe, to the 100% homologous chromosomal gene in *E. coli*, the entire library was harvested from the petri dishes by flooding them with phosphate buffered saline and using a glass rod to dislodge the colonies, and the resulting bacterial population was subjected to a large-scale plasmid isolation, resulting in an amplified *Salmonella* library plasmid pool. This plasmid pool was then transformed to *Salmonella* LT2 YS5010, thereby eliminating the *E. coli* background.

A probe for msbB homologues was generated using a clone of the *E. coli* msbB gene (Karow and Georgopoulos 1992 J. Bacteriol. 174: 702-710) by digesting *E. coli* with BglII/HincII and isolating a 600 bp fragment which corresponds to a portion of the coding sequence. This fragment was labeled using $\alpha^{32}$P-dCTP and used to probe the *Salmonella* library at low-stringency conditions consisting of 6×SSC, 0.1% SDS, 2× Denhardts, 0.5% non-fat dry milk overnight at 55° C. Strongly hybridizing colonies were purified, and plasmids extracted and subjected to restriction digestion and in situ gel hybridization under the same conditions used for colony hybridization (Ehtesham and Hasnain 1991 BioTechniques 11: 718-721). Further restriction digests revealed a 1.5 kB fragment of DNA which strongly hybridized with the probe and was sequenced at the Yale University Boyer Center using fluorescent dye termination thermal cycle sequencing. Sequence analysis revealed that the 1.5 kb fragment contained an msbB homologue which apparently lacked an initiating methionine corresponding to that of the *E. coli* gene. A probe consisting of the 5' region of this clone was generated by performing restriction digests using EcoRI/XbaI and again hybridizing to the library. The complete nucleotide sequence of the *Salmonella* msbB gene (SEQ ID NO:1) and the deduced amino acid sequence of the encoded protein (SEQ ID NO:2) is shown in FIGS. 1A-1B. The DNA homology of the putative *Salmonella* msbB and the *E. coli* msbB is 75%. The protein homology is 98%, confirming that the cloned *Salmonella* gene is a bona fide msbB.

7.2. Genetic Alteration of *Salmonella* msbB

A knockout construct was generated using the cloned *Salmonella* msbB gene. The cloned gene was cut with SphI and MluI, thereby removing approximately half of the msbB coding sequence, and the tetracycline resistance gene from pBR322, cut with AatII and AvaI, was inserted after blunt-ending using the Klenow fragment of DNA polymerase I (FIGS. 2A-2C). The knockout disruption was accomplished by homologous recombination procedures (Russell et al., 1989, J. Bacteriol. 171:2609); the construct was linearized using SacI and KpnI, gel purified and transfected to *Salmonella* LT2 YS501 by electroporation. Bacteria from the transformation protocol were first selected on tetracycline plates, and subsequently examined for the presence of plasmid-containing non-chromosomal integrated contaminants by ampicillin resistance and the presence of plasmids as determined by standard plasmid mini-preps (Titus, D. E., ed. *Promega Protocols and Applications Guide*, Promega Corp, 1991). Bacterial colonies which were tetracycline resistant yet lacked plasmids were subjected to a PCR-based analysis of the structure of their msbB gene. PCR was used with primers which generate a fragment inclusive of the region into which the tetracycline gene was inserted, where the forward primer was GTTGACTGGGAAGGTCTGGAG (SEQ ID NO:3), corresponding to bases 586 to 606, and the reverse primer was CTGACCGCGCTCTATCGCGG (SEQ ID NO:4), corresponding to bases 1465 to 1485. Wild type *Salmonella* msbB+ results in an approximately 900 base pair product, whereas the disrupted gene with the tetracycline insert results in an approximately 1850 base pair product. Several clones were obtained where only the larger PCR product was produced, indicating that the disruption in the msbB gene had occurred.

Southern blot analysis was used to confirm the disruption of the chromosomal copy of *Salmonella* msbB. The plasmid-based knockout construct (KO) was compared with genomic DNA prepared from wild type and putative disrupted msbB clones, YS82, YS86, YS8211 and YS861. The DNA was double digested with AseI/BamH1 and separated by agarose gel electrophoresis on 0.9% or 1.2% agarose. Results of YS8211 and YS861 are presented in FIGS. 3A-3C. Similar gels were subjected to three separate criteria: 3A) the presence of the tetracycline gene when probed with an $^{32}$P-labeled tetracycline gene fragment, 3B) Restriction fragment length when probed with an $^{32}$P-labeled AseI/BamH1 fragment derived from the cloned msbB and 3C) the presence or absence of the msbB mluI fragment removed in order to disrupt the msbB gene and insert the tetracycline gene (FIGS. 3A-3C). Since the mluI fragment was removed in order to disrupt the msbB gene and insert the tetracycline gene, it is expected that this probe would hybridize with the wild type FIG. 3C (lane 2 WT) but not the knockout construct (lane 1 KO), or the clones, (lanes 3 and 4 YS8211 and YS821) thereby confirming the genetic alteration of the msbB gene. Each of the clones examined exhibited all of the expected criteria for an msbB gene deletion (knockout). These data further confirm that msbB exists as a single copy in the wild type *Salmonella*, as no other hybridizing bands were observed when probed with a labeled oligonucleotide derived from the cloned DNA.

After the msbB mutation was confirmed, additional strains containing the msbB⁻ mutation were generated. The *Salmonella* strains used included WT 14028 and YS72 (pur⁻ xyl⁻ hyperinvasive mutant from WT 14028; Pawelek et al., WO 96/40238). P22 transduction was used to generate YS8211 (msbB::tet) using YS82 as a donor and YS861 and YS862 (msbB1::tet) using YS86 as a donor; all with WT 14028 as recipient. YS7216 (msbB1::tet from YS72) was generated by transduction using YS82 as a donor. Several derivatives are encompassed by the present invention, including but not limited to derivatives of YS8211 (YS8212, YS1170), YS862 (YS8644, YS8658), and YS7216 (YS1601, YS1604, YS1629). In a preferred embodiment, spontaneous derivatives grow somewhat faster on Luria agar compared to WT 14028 or msbB⁻ clones generated by transduction. msbB⁺ strains were grown in LB broth or on LB plates containing 1.5% agar at 37° C. msbB⁻ strains were grown in modified LB containing 10 g tryptone, 5 g yeast extract, 2 ml 1N $CaCl_2$ and 2 ml 1N $MgSO_4$ per liter, adjusted to pH 7 using 1N NaOH. For transducing msbB1::tet, LB lacking NaCl was used, with 4 mg/l tetracycline. Liquid cultures were shaken at 225 rpm. For tumor targeting experiments, cells were diluted 1:100 in LB, grown to $OD_{600}$=0.8 to 1.0, washed in phosphate buffered saline (PBS), and resuspended in PBS.

7.3. Disruption of *Salmonella* msbB Reduces TNFα Induction

7.3.1. TNFα Induction in Mice

WT 14028 and the msbB⁻ clone YS8211, were first grown to saturation in LB media at 37° C. with shaking at 225 rpm. A 1:100 dilution of these bacterial strains were then transferred to fresh LB and grown to an $OD_{600}$=1.0 at 37° C. with shaking at 225 rpm. The bacteria were diluted in phosphate buffered saline and $1.0 \times 10^8$ c.f.u. (about $5 \times 10^9$ c.f.u./kg) were injected into the tail vein of Balb/C mice (n=4/strain), with PBS as a negative control. After 1.5 hours, serum was harvested in triplicate samples by cardiac puncture, centrifuged to remove the cellular content, and analyzed for TNFα using a Biosource International Cytoscreen ELISA plate, which was read on a Molecular Devices Emax microplate reader.

Results are presented in FIG. 4 and expressed as a percent of the level of TNFα induced by wild type *Salmonella*.

As demonstrated in FIG. 4, YS8211 induced TNFα significantly less than WT 14028. Thus, as shown in FIG. 4, the msbB⁻ strain induced TNFα about 33% (i.e., 3 times less) of the wild type msbB⁺ strain.

7.3.2. TNFα Induction in Pigs

An msbB⁻ strain of *Salmonella*, YS8212, and WT 14028, were first grown to saturation in LB media at 37° C. with shaking at 225 rpm. A 1:100 dilution of these bacterial strains were then transferred to fresh LB and grown to an $OD_{600}$=0.8 at 37° C. with 225 rpm. The bacteria were washed in phosphate buffered saline and $1.0 \times 10^9$ c.f.u. (about $1 \times 10^8$ c.f.u./kg) were injected into the ear vein of Sinclair swine (n=6/strain). After 1.5 and 6.0 hours, serum was harvested, centrifuged to remove the cellular content, and frozen for later analysis. Analysis for TNFα utilized a Genzyme Predicta ELISA plate, which was read using a Gilson spectrophotometer.

Results are presented in FIG. 5 and are expressed as picograms of TNFα/ml serum.

As demonstrated in FIG. 5, at 90 minutes the level of TNFα induced by the msbB⁻ strain was significantly lower than that induced by the *Salmonella* WT 14028.

7.3.3. *Salmonella* LPS-Induced Respiration in Pigs

Lipopolysaccharide (LPS) from *Salmonella* WT 14028 and the msbB⁻ clone, YS8212 was prepared using the procedure described by Galanos et al. (1969 Eur. J. Biochem. 9: 245-249). Briefly, LPS was extracted from bacteria which had been grown to $OD_{600}$ of 1.0. The bacteria were pelleted by centrifugation, washed twice with distilled water and frozen at −20 C. LPS was purified by extraction with a mixture of 18.3 ml H20:15 ml phenol in a shaking water bath for 1 hr at 70 C. The mixture was cooled on ice, centrifuged at 20,000×g for 15 min, and the aqueous phase was removed. LPS was precipitated from the aqueous phase by addition of NaCl to 0.05 M and 2 volumes ethanol and incubation on ice, followed by centrifugation of 2000×g for 10 min. The precipitation was repeated after redissolving the pellet in 0.05 M NaCl, and the pellet lyophilized. The LPS was dissolved in sterile distilled water, and either 5 μg/kg or 500 μg/kg LPS was injected into the ear vein of Sinclair-swine which had been anesthetized with Isoflurane. After 1.5 and 6.0 hours, respiration rate was determined and recorded.

Results are presented in FIGS. 6A-6B and are expressed as a percentage of respiration at time zero ($t_0$).

As demonstrated in FIGS. 6A-6B, respiration was significantly higher in the pigs administered wild type LPS as compared to those administered the LPS from the msbB⁻ strain. Thus, disruption of the msbB gene in *Salmonella*, produces a modification in lipid A which results in reduced ability to increase respiration.

7.3.4. TNFα Induction in Human Monocytes

Human monocytes were prepared from peripheral blood by centrifugation through Isolymph (Pharmacia) and allowed to adhere to 24 well plates containing RPMI 1640. *Salmonella* WT 14028 and several of the msbB⁻ 14028 strains (YS8211, YS8212, YS8658, and YS1170) were first grown to saturation in LB media at 37° C. with shaking at 225 rpm. A 1:100 dilution of these bacterial strains was then transferred to fresh LB and grown to an $OD_{600}$=0.8 at 37° C. with 225 rpm. The bacteria were added to the cell culture wells and the culture medium was harvested after 2.0 hours, centrifuged to remove the cellular content, and analyzed for TNFα using a Genzyme Predicta ELISA plate, which was read using a Gilson spectrophotometer.

The data are presented in FIG. 7 and expressed as picograms of TNFα/ml serum.

As demonstrated in FIG. 7, the msbB⁻ strains induced TNFα significantly less than did the wild type strain.

7.3.5. msbB− *Salmonella* LPS TNFα Induction in Human Monocytes

Human monocytes were prepared from peripheral blood by centrifugation through Isolymph (Pharmacia) and allowed to adhere to 24 well plates containing RPMI 1640. Lipopolysaccharide (LPS) of wild type and of a number of msbB⁻ mutant *Salmonella*, (i.e., YS8211, YS8212, YS8658 and YS1170) was prepared using the procedure described by Galanos et al. (1969 Eur. J. Biochem. 9: 245-249) (see Section 7.3.3 for a brief description). The LPS was dissolved in sterile distilled water, and quantities ranging from 0.001 to 100 ng/ml LPS were added to the cell culture wells. After 15 hours the culture medium was harvested, centrifuged to remove the cellular content, and analyzed for TNFα using a Genzyme Predicta ELISA plate, which was read using a Gilson spectrophotometer.

The data are presented in FIG. 8 and are expressed as picograms of TNFα/ml serum.

As demonstrated in FIG. 8, LPS purified from the msbB⁻ strains induced TNFα significantly less than did the LPS from the wild type strain.

7.4. Disruption of *Salmonella* msbB Reduces Virulence

7.4.1. In Mice

A culture of wild type *Salmonella* 14028 and one of its msbB⁻ *Salmonella* clones, YS862, were grown in LB medium lacking sodium chloride at 37° C. with shaking at 250 rpm until the cultures reached an $OD_{600}$ of 0.8. The bacteria were diluted into phosphate buffered saline (PBS) at a ratio of 1:10 and the equivalent of $2 \times 10^7$ c.f.u. were injected i.p. into C57BL/6 mice bearing B16F10 melanomas. Survival was determined daily, or at two to four day intervals.

Results are presented in FIG. 9A and are expressed as percent survival.

As shown in FIG. 9A, WT 14028 killed all the mice in 4 days, whereas the msbB⁻ mutant spared 90% of the mice past 20 days, demonstrating a significant reduction in virulence by the msbB⁻ mutant.

7.4.2. In Pigs

A culture of WT 14028 and one of its msbB⁻ *Salmonella* clones, YS8212, were grown in LB medium lacking sodium chloride at 37° C. with shaking of 250 RPM until the cultures reached an $OD_{600}$ of 0.8. The bacteria were washed in phosphate buffered saline and $1.0 \times 10^9$ were injected into the ear vein of Sinclair swine (n=4/strain). Survival was determined daily, or at two to four day intervals.

Results are presented in FIG. 9B and are expressed as percent survival.

As shown in FIG. 9B, WT 14028 killed all the swine in 3 days, whereas the msbB⁻ mutant spared 100% of the mice past 20 days, demonstrating a significant reduction in virulence.

7.5. Tumor Targeting

7.5.1. msbB Mutation

*Salmonella* WT 14028 with the msbB⁻ modification, were assayed to determine if they possessed tumor targeting ability using the B16F10 melanoma subcutaneous animal model. The msbB⁻ clone, YS8211, was grown in LB media lacking sodium chloride at 37° C. with shaking at 250 rpm to an $OD_{600}$ of 0.8. An aliquot of $2.0 \times 10^6$ c.f.u. was injected i.v. into C57BL/6 mice which had been implanted with $2 \times 10^5$ B16 melanoma cells 16 days prior to the bacterial infection. At two days and five days post bacterial infection, mice were sacrificed and tumors and livers assayed for the presence of the bacteria by homogenization and plating of serial dilutions.

Results are presented in FIG. 10 and are expressed as c.f.u. bacteria/g tissue. As demonstrated in FIG. 10, a positive ratio of tumor to liver (700:1) was found at 2 days, and increased to a positive ratio of 2000:1 at 5 days. Thus, the msbB⁻ mutant maintained the ability to target to a solid cancer tumor.

7.5.2. msbB Mutation in Combination with Auxotrophic Mutation

In order to assess compatibility with auxotrophic mutations, as measured by retention of the ability to target and replicate within tumors, combinations of the msbB mutation with auxotrophic mutations were generated. msbB⁺ strains were grown in LB broth or LB plates containing 1.5% agar at 37°. msbB⁻ strains were grown in modified LB containing 10 g tryptone, 5 g yeast extract, 2 ml 1N CaCl₂ and 2 ml 1N MgSO₄ per liter, adjusted to pH 7 using 1N NaOH. For transducing msbB1::tet, LB lacking NaCl was used, with 4 mg/l tetracycline. Liquid cultures were shaken at 225 rpm. The msbB1::tet was transduced to auxotrophic strains to generate YS1604 (msbB⁻, pur⁻, hyperinvasive), YS7232 (msbB⁻, purI⁻, hyperinvasive), YS7244 (msbB⁻, purI⁻, AroA⁻ hyperinvasive), YS1482 (msbB⁻, purI⁻, purA⁻). For tumor targeting experiments, cells were diluted 1:100 into LB, grown to $OD_{600}$=0.8 to 1.0, washed in phosphate buffered saline (PBS), resuspended in PBS, and $2 \times 10^6$ were injected into the tail vein of C57BL/6 mice. At day 7, tumors were excised, weighed, homogenized, and c.f.u. determined by plating serial dilutions onto modified LB described above.

Results are presented in Table I and are expressed as c.f.u. per gram tumor tissue. Some of the strains, YS8211, YS1604, and YS7232 show high levels of c.f.u. within the tumors, whereas YS7244 and YS1482 are approximately 500 to 5000 times less.

TABLE I

| Strain | genetic marker | c.f.u./gram tumor tissue |
|---|---|---|
| YS8211 | msbB⁻ | $3 \times 10^9$ |
| YS1604 | msbB⁻, pur⁻, hyperinvasive | $9 \times 10^9$ |
| YS7232 | msbB⁻, purI⁻, hyperinvasive | $9 \times 10^9$ |
| YS7244 | msbB⁻, purI⁻, AroA⁻ hyperinvasive | $5 \times 10^5$ |
| YS1482 | msbB⁻, purI⁻, purA⁻ | $6 \times 10^6$ |

7.6. Use of *Salmonella* with Disrupted msbB for Anti-Tumor Activity In Vivo

*Salmonella typhimurium* 14028 msbB⁻ clones YS8211, YS8212, YS7216, and YS1629 and WT 14028 (control) were grown in LB media lacking sodium chloride at 37° C. with shaking at 250 rpm to an $OD_{600}$ of 0.8. An aliquot of $2.0 \times 10^6$ c.f.u. was injected i.p. into C57BL/6 mice which had been implanted with $2 \times 10^5$ B16 melanoma cells 8 days prior to the bacterial infection. Tumor volume was monitored over time.

Results are presented in FIG. 11. Two of the strains, YS8211 and YS1629, showed significant tumor retardation, i.e., tumor growth inhibition.

7.7. Increased Sensitivity to Chelating Agents

In order to assess the sensitivity of bacterial strains to chelating agents, bacteria with or without the msbB mutation were grown in the presence or absence of 1 mM EDTA or 10 mM sodium citrate in Luria Broth (LB) lacking sodium chloride. An overnight culture of each of the bacterial strains was diluted 1 to 100 in fresh media, and grown at 37° C. with shaking at 250 rpm. The effect on growth was determined by spectrophotometric readings at an $OD_{600}$.

WT 14028 and msbB⁻ clone YS8211 were grown in the presence or absence of 1 mM EDTA (FIG. 12A). EDTA did not inhibit the growth of WT 14028. In contrast, the msbB⁻ clone showed near complete cessation of growth after 3 hours in the presence of EDTA.

WT 14028 and msbB⁻ clone YS862 were grown in the presence and absence of 10 mM sodium citrate (FIG. 12B). The msbB⁺ WT 14028 strain showed little inhibition by sodium citrate compared to the msbB⁻ strain which showed near complete cessation of growth after 3 hours in the presence of sodium citrate.

Thus, the msbB⁻ *Salmonella* mutants exhibited sensitivity to chelating agents which promote eradication of the bacteria, a characteristic which is similar to an antibiotic effect. It is envisioned that such a characteristic would be advantageous for use of msbB⁻ *Salmonella* mutants for in vivo therapy.

In order to further assess the sensitivity of *Salmonella* strains to chelating agents, the hyperinvasive pur strain YS72, its msbB⁻ strain, YS721, and a derivative of YS7216, YS1629, were grown in the presence of increasing concentrations of EDTA. The number of c.f.u. was determined after 4 hours. A fresh culture of YS72, its msbB⁻ strain YS7216 and its faster-growing derivative YS1629 were diluted 1 to 100 in fresh, zero salt LB media containing 0, 0.25, 0.5, 1.0 or 2.0 mM EDTA and grown at 37° C. with 225 RPM for 4 hours, and c.f.u. was determined by plating serial dilutions onto LB plates (Table II). Greater than 99% inhibition was achieved for the msbB⁻ strain YS7216 at concentrations of EDTA greater than 0.25 mM and its derivative YS1629 was inhibited greater than 90% at 0.5 mM and greater than 99% at 2.0 mM. In contrast, although the YS72 clone exhibited some sensitivity to EDTA it was no inhibited at the 90% level even at 2.0 mM.

TABLE II

| Strain | c.f.u. no EDTA | c.f.u. + EDTA {% inhibition} | | | |
|---|---|---|---|---|---|
| | | [0.25 mM] | [0.5 mM] | [1.0 mM] | [2.0 mM] |
| YS72 | $3.0 \times 10^9$ | $2.4 \times 10^9$ {20%} | $1.5 \times 10^9$ {50%} | $7.3 \times 10^8$ {75%} | $4.8 \times 10^8$ {84%} |
| YS7216 | $6.3 \times 10^8$ | $2.1 \times 10^6$ {99.6%} | $1.1 \times 10^6$ {99.8%} | $3.2 \times 10^6$ {99.4%} | $4.3 \times 10^6$ {99.3%} |
| YS1629 | $1.3 \times 10^9$ | $6.0 \times 10^8$ {54%} | $1.0 \times 10^8$ {92%} | $2.9 \times 10^7$ {97%} | $7.5 \times 10^6$ {99.4%} |

8. Bacterial Survival within Macrophages

In order to determine the sensitivity of msbB⁻ *Salmonella* to macrophages, two types of macrophages were used: (A) bone marrow-derived macrophages obtained from the femurs and tibias of C57BL/6 mice, which were allowed to replicate by addition of supernatant from the LADMAC cell line which secretes macrophage colony stimulating factor (Sklar et al., 1985. J. Cell Physiol. 125:403-412) and (B) J774 cells (a murine macrophage cell line) obtained from America Type Culture Collection (ATCC). *Salmonella* strains used were WT 14028 and its msbB⁻ derivatives YS8211 and YS1170. Bacteria were grown to late log phase $OD_{600}=0.8$ and $1 \times 10^6$ were allowed to infect a confluent layer of mammalian cells within a 24 well dish for 30 min, after which the extracellular bacteria were removed by washing with culture medium and the addition of 50 mg/ml gentamicin (Elsinghorst, 1994, Methods Enzymol. 236:405-420). Bacteria were counted by plating serial dilutions of the cell layer removed using 0.01% deoxycholate, and expressed as the percent initial c.f.u. over time.

The results are presented in FIGS. 13A-13B and expressed as percent c.f.u. per time. The msbB⁻ strain shows significantly less survival in macrophages.

9. LD50 of MsbB Derivatives

Spontaneous derivatives of msbB⁻ strains YS8211 and YS7216 were selected from in vitro culture on non-modified LB medium based upon enhanced growth characteristics. These bacterial strains were grown to $OD_{600}$ of 0.8 and c.f.u. ranging from $1 \times 10^2$ to $1 \times 10^8$ were injected i.v. into the tail vein of C57BL/6 mice. Acute lethality was determined at 3 days, and the $LD_{50}$ determined as described by Welkos and O'Brien (Methods in Enzymology 235:29-39, 1994). The results are presented in Table III. Thus, although all the msbB⁻ strains have a reduced ability to induce TNFα (See Section 7.3.5), the results demonstrate that strain YS1170 is significantly less attenuated than other msbB⁻ strains and therefore not all msbB⁻ strains are useful for providing both reduced TNFα induction and reduced virulence.

TABLE III

| Strain | $LD_{50}$ |
|---|---|
| WT 14028 | $1 \times 10^3$ |
| YS8211 | $4 \times 10^6$ |
| YS8212 | $3.9 \times 10^7$ |
| YS1629 | $1 \times 10^7$ |
| YS1170 | $1 \times 10^6$ |

10. Deposit of Microorganisms

The following microorganisms were deposited with the American Type Culture Collection (ATCC), 12301 Parklawn Drive, Rockville, Md. 20852 on Sep. 9, 1997 and have been assigned the indicated Accession numbers:

| Microorganism | ATCC Accession No. |
|---|---|
| YS8211 | 202026 |
| YS1629 | 202025 |
| YS1170 | 202024 |

The invention claimed and described herein is not to be limited in scope by the specific embodiments, including but not limited to the deposited microorganism embodiments, herein disclosed since these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A mutant *Salmonella* sp. comprising a disrupted msbB gene in which the mutant *Salmonella* targets solid tumor when administered in vivo.

2. The mutant *Salmonella* of claim 1 which is designated YS1629 and having ATCC Accession No. 202025 or is designated YS1170 and having ATCC Accession No. 202024 or is designated YS8211 and having ATCC Accession No. 202026.

3. The mutant *Salmonella* of claim 1 which is selected from the group consisting of *Salmonella typhi, Salmonella choleraesuis*, and *Salmonella enteritidis*.

4. The mutant *Salmonella* of claim 1 which expresses an altered lipid A molecule.

5. The mutant *Salmonella* of claim 1 which induces TNF-$\alpha$ expression at about 5 percent to about 40 percent of that induced by a wild type *Salmonella* sp.

6. The mutant *Salmonella* of claim 1 which induces TNF-$\alpha$ expression at about 10 percent to about 35 percent of that induced by a wild type *Salmonella* sp.

7. The mutant *Salmonella* of claim 1 in which a chelating agent inhibits growth by about 90 percent compared to the growth of a wild type *Salmonella* sp.

8. The mutant *Salmonella* of claim 1 in which a chelating agent inhibits growth by about 99 percent compared to the growth of a wild type *Salmonella* sp.

9. The mutant *Salmonella* of claim 1 in which a chelating agent inhibits growth greater than 99 percent compared to the growth of a wild type *Salmonella* sp.

10. The mutant *Salmonella* of claim 1 which survives in macrophages at about 50 percent to about 30 percent of the level of survival of a wild type *Salmonella* sp.

11. The mutant *Salmonella* of claim 1 which survives in macrophages at about 30 percent to about 10 percent of the level of survival of a wild type *Salmonella* sp.

12. The mutant *Salmonella* of claim 1 which survives in macrophages at about 10 percent to about 1 percent of the level of survival of a wild type *Salmonella* sp.

* * * * *

UNITED STATES PATENT AND TRADEMARK OFFICE
CERTIFICATE OF CORRECTION

PATENT NO. : 7,514,089 B2
APPLICATION NO. : 11/117085
DATED : April 7, 2009
INVENTOR(S) : Bermudes et al.

It is certified that error appears in the above-identified patent and that said Letters Patent is hereby corrected as shown below:

On page 2 of the patent, under category (56), under FOREIGN PATENT DOCUMENTS:
"IL 124936 7/2000" should be --IL 134936 7/2000--

Insert the following reference under category (56), OTHER PUBLICATIONS, which starts on page 2:
--Israeli Notice of Allowance for Israeli Patent No. 122407, Filed February 12, 1997, Dated September 20, 2007.--

On page 3 of the patent, under category (56), OTHER PUBLICATIONS:
"U.S. Office Action for King et al., U.S. Appl. No. 10/738,423, Filed Dec. 16, 2003, dated June 28, 2006." should be --U.S. Office Action for King et al., U.S. Appl. No. 10/738,423, Filed Dec. 16, 2003, dated June 28, 2007.--

On page 4 of the patent, under category (56), OTHER PUBLICATIONS:
"U.S. Notice of Allowance for Bermudes et al., U.S. Appl. No. 09/337,689, filed June 22, 1999, Dated Feb. 27, 2001." should be --U.S. Office Action for Bermudes et al., U.S. Appl. No. 09/337,689, filed June 22, 1999, Dated Feb. 27, 2001.--

On page 4 of the patent, under category (56), OTHER PUBLICATIONS:
"U.S. Notice of Allowance for Bermudes et al., U.S. Appl. No. 09/337,689, filed June 22, 1999, Dated Oct. 9, 2001." should be --U.S. Office Action for Bermudes et al., U.S. Appl. No. 09/337,689, filed June 22, 1999, Dated Oct. 9, 2001.--

On page 5 of the patent, under category (56), OTHER PUBLICATIONS:
"Bonneoh, et al., 1995, 'Inhibition of Melanoma Growth by Adenoviral-Mediated HSV Thymidine Kinase Gene Transfer in vivo,' J. Invest. Derm., 104:313-317." should be --Bonnekoh, et al., 1995, "Inhibition of Melanoma Growth by Adenoviral-Mediated HSV Thymidine Kinase Gene Transfer in vivo," J. Invest. Derm. 104:313-317.--

On page 6 of the patent, under category (56), OTHER PUBLICATIONS:
"Lemmon, et al., 1997, 'Anaerobic Bacteria as a Gene Delivery System that is Controlled by the Tumor Microenvironment,' Gene Therapy, 4: 79-796." should be --Lemmon, et al., 1997, "Anaerobic Bacteria as a Gene Delivery System that is Controlled by the Tumor Microenvironment," Gene Therapy, 4: 791-796.--

UNITED STATES PATENT AND TRADEMARK OFFICE
CERTIFICATE OF CORRECTION

PATENT NO.       : 7,514,089 B2
APPLICATION NO.  : 11/117085
DATED            : April 7, 2009
INVENTOR(S)      : Bermudes et al.

It is certified that error appears in the above-identified patent and that said Letters Patent is hereby corrected as shown below:

On page 6 of the patent, under category (56), OTHER PUBLICATIONS:
"Schaer, et al., 1992, 'Induction of a Cellular Immune Response to a Foreign Antigen by a Recombinant Listeria monocytogenes Vaccine,' J. Immunol. 149:53-59." should be --Schafer, et al., 1992, "Inducation of a Cellular Immune Response to a Foreign Antigen by a Recombinant Listeria monocytogenes Vaccine," J. Immunol. 149:53-59.--

On page 8 of the patent, under category (56), OTHER PUBLICATIONS:
"Coley, William B., Jan. 1991, 'The Treatment of Malignant Tumors by Repeated Inoculations of Erysipelas with a Report of Ten Original Cases,' Clinical Orthopaedics and Related Research, vol. 262:3-11. Abridged from Coley, W.B.: The treatment of malignant tumors by repeated inoculations of erysipelas: With a report of ten original cases. Am. J. Med. Sci. vol. 105;487:1983." should be --Coley, William B., Jan. 1991, "The Treatment of Malignant Tumors by Repeated Inoculations of Erysipelas with a Report of Ten Original Cases," Clinical Orthopaedics and Related Research, vol. 262:3-11. Abridged from Coley, W.B.: The treatment of malignant tumors by repeated inoculations of erysipelas: With a report of ten original cases. Am. J. Med. Sci. vol. 105;487:1893.--

Signed and Sealed this

Ninth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,514,089 B2  Page 1 of 1
APPLICATION NO. : 11/117085
DATED : April 7, 2009
INVENTOR(S) : Bermudes et al.

It is certified that error appears in the above-identified patent and that said Letters Patent is hereby corrected as shown below:

On the title page, item (73), ASSIGNEE, please insert --Yale University, New Haven, CT (US)--

Signed and Sealed this

Fifteenth Day of September, 2009

David J. Kappos
*Director of the United States Patent and Trademark Office*